United States Patent
Ko et al.

(10) Patent No.: US 11,141,444 B2
(45) Date of Patent: Oct. 12, 2021

(54) LACTOBACILLUS CRISPATUS KBL693 STRAIN AND USE THEREOF

(71) Applicant: KO Biolabs, Inc., Seoul (KR)

(72) Inventors: Woo Ri Ko, Seoul (KR); June Chul Lee, Gyeonggi-do (KR); Tae-Wook Nam, Gyeonggi-do (KR); Gwang Pyo Ko, Seoul (KR); Hyun Ju You, Incheon (KR); So Yon Yoon, Gyeonggi-do (KR); Seok Cheon Song, Seoul (KR)

(73) Assignee: KO Biolabs, Inc., Seoul (KR)

( * ) Notice: Subject to any disclaimer, the term of this patent is extended or adjusted under 35 U.S.C. 154(b) by 0 days.

(21) Appl. No.: 17/102,243

(22) Filed: Nov. 23, 2020

(65) Prior Publication Data

US 2021/0106631 A1   Apr. 15, 2021

Related U.S. Application Data

(63) Continuation of application No. PCT/KR2019/006231, filed on May 23, 2019.

(30) Foreign Application Priority Data

May 23, 2018 (KR) ........................ 10-2018-0058569

(51) Int. Cl.
| | |
|---|---|
| *A61K 35/747* | (2015.01) |
| *A23L 33/135* | (2016.01) |
| *A61P 11/06* | (2006.01) |
| *A61P 37/08* | (2006.01) |
| *A61P 31/10* | (2006.01) |
| *A61K 8/99* | (2017.01) |

(52) U.S. Cl.
CPC .......... *A61K 35/747* (2013.01); *A23L 33/135* (2016.08); *A61K 8/99* (2013.01); *A61P 11/06* (2018.01); *A61P 31/10* (2018.01); *A61P 37/08* (2018.01)

(58) Field of Classification Search
None
See application file for complete search history.

(56) References Cited

U.S. PATENT DOCUMENTS

2003/0049231 A1   3/2003   Baur et al.

FOREIGN PATENT DOCUMENTS

| KR | 1014872100000 | 2/2015 |
| KR | 1020160123983 | 10/2016 |
| WO | 2006/013441 | 2/2006 |

OTHER PUBLICATIONS

Ahmadjian, Vernon, Moore, David and Alexopoulos, Constantine John. "Fungus". Encyclopedia Britannica, Feb. 27, 2020, https://www.britannica.com/science/fungus. Accessed Apr. 5, 2021.*
International SReport on Patentability for International Application No. PCT/KR2019/006231, "Lactobacillus Crispatus KBL693 Strain and Use Thereof" dated Nov. 24, 2020.
Written Opinion for International Application No. PCT/KR2019/006231, "Lactobacillus Crispatus KBL693 Strain and Use Thereof" dated Aug. 27, 2019.
Kim K et al, "Inhibitory mechanism of anti-allergic peptides in RBL2H3 cells", Eur J Pharmacol, 581:191-203, 2008.
Tobita, K., et al., "Anti-allergic effects of Lactobacillus crispatus KT-11 strain on ovalbumin-sensit ized BALB/c mice", dissertation, 25 pages (2010).
International Search Report for International Application No. PCT/KR2019/006231, "Lactobacillus Crispatus KBL693 Strain and Use Thereof" dated Aug. 27, 2019.
Ko, W., "Inhibitory effects of Lactobacillus crispatus isolated from vaginal microbiota on atopic dermatitis", Dept. of Environmental Health, The Graduate School of Public Health, Seoul National University, Actual publication date Feb. 7, 2019 (53 pages).

* cited by examiner

*Primary Examiner* — Oluwatosin A Ogunbiyi
(74) *Attorney, Agent, or Firm* — Hamilton, Brook, Smith & Reynolds, P.C.

(57) ABSTRACT

A strain of *Lactobacillus crispatus* KBL693 and the use thereof are disclosed. The strain of *Lactobacillus crispatus* KBL693 (Accession No. KCTC 13519BP) attenuates allergic reactions of cells, significantly improves symptoms of atopic dermatitis, and exhibits anti-inflammatory and anti-fungal effects. Thus, the single strain alone can achieve all the purposes of alleviating atopic dermatitis and other allergic diseases and improving inflammatory diseases and autoimmune diseases, thereby finding advantageous applications as a probiotic substance. In addition, the strain, based on the anti-fungal activity thereof, can be advantageously utilized in a skin external preparation against various skin diseases caused by fungi, and in a cosmetic composition and a functional patch for alleviating sensitive skin.

15 Claims, 10 Drawing Sheets

Specification includes a Sequence Listing.

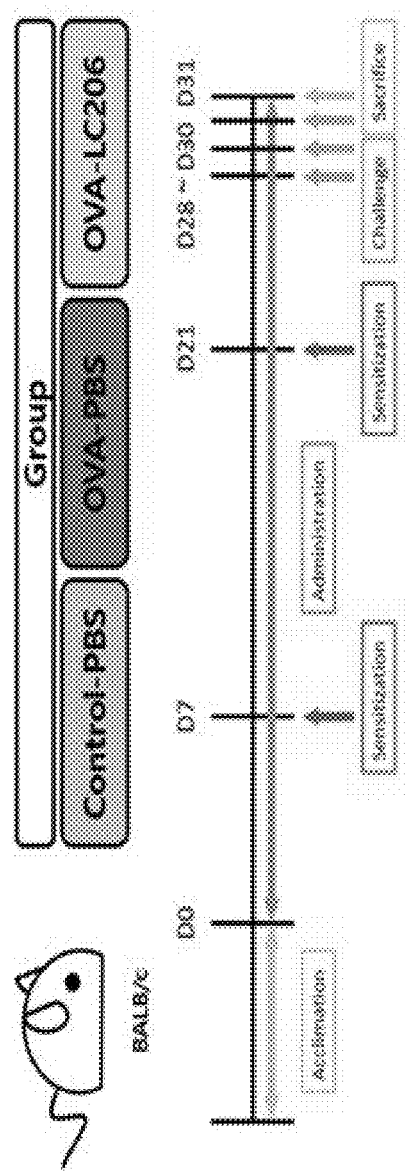
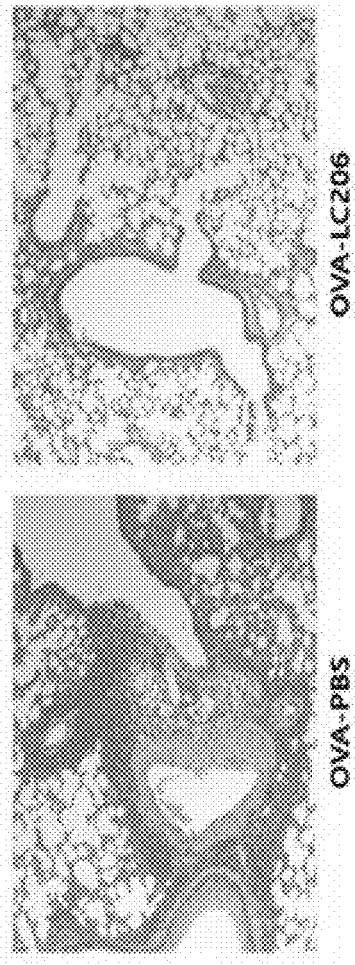
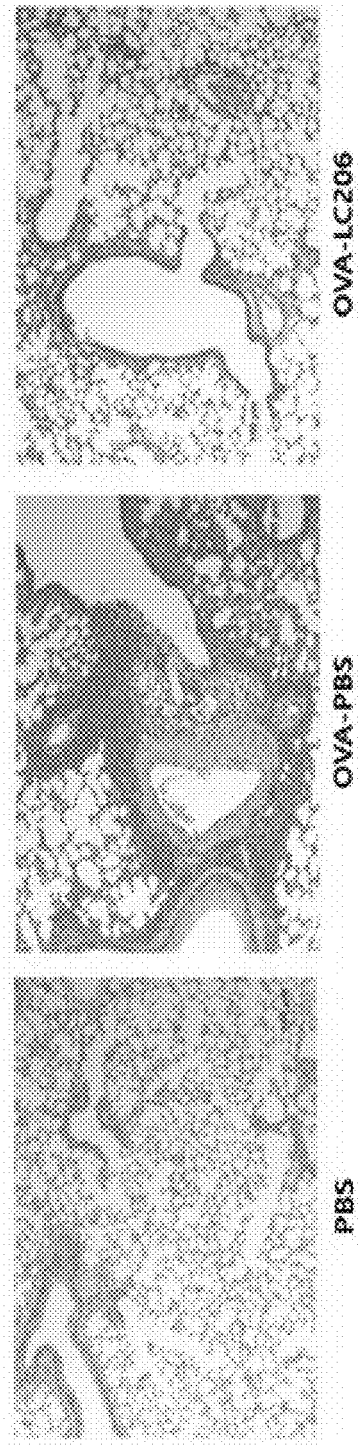
FIG. 13A
FIG. 13B
FIG. 13C
FIG. 13D

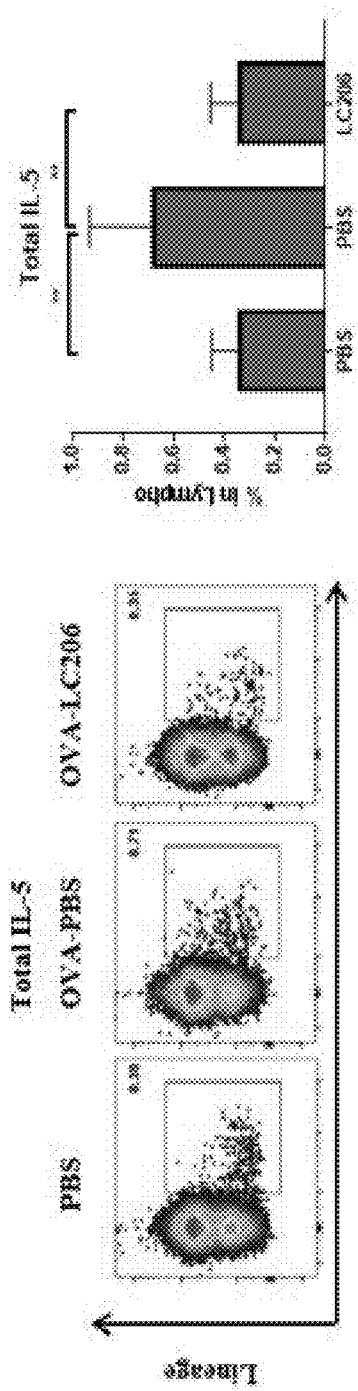
FIG. 14A
FIG. 14C
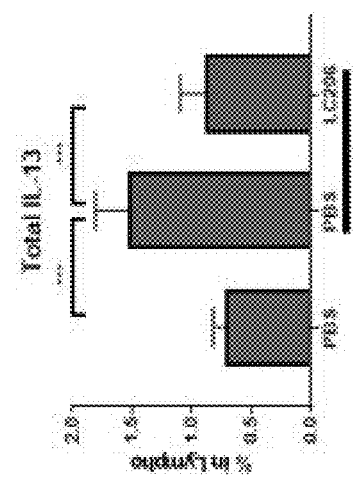
FIG. 14B
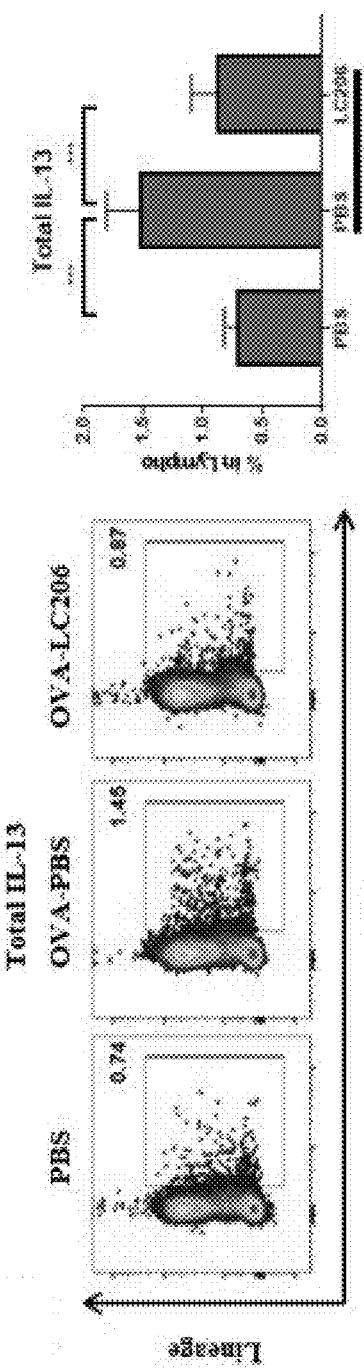
FIG. 14D

LACTOBACILLUS CRISPATUS KBL693 STRAIN AND USE THEREOF

RELATED APPLICATIONS

This application is a continuation of International Application No. PCT/KR2019/006231, which designates the United States and was filed on May 23, 2019, published in Korean and claims priority under 35 U.S.C. § 119 or 365 to Korean Application No. 10-2018-0058569, filed May 23, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 58881001001_SEQUENCELISTING.txt; created Nov. 19, 2020, 3 KB in size.

BACKGROUND ART

Probiotics refer to microorganisms and the resulting products therefrom having antimicrobial activities and enzyme activities to help the balance of intestinal microorganisms. In addition, probiotics are also defined as live bacteria in the form of a single or multiple strain(s) to improve intestinal flora when provided to human or animals in the form of dry cells or fermentation products. Probiotics must inhabit the human gut, be non-pathogenic and non-toxic, and survive long enough until they arrive at the intestine. Further, probiotics must maintain viability and activities until they are consumed in the food delivered, be sensitive to antibiotics used to prevent infection and do not have antibiotic-resistant plasmids. Also, probiotics must be resistant to acids, enzymes, and bile in the intestinal environment.

These probiotics may include, for example, *Bacillus* sp. having an excellent ability to produce digestive enzymes such as amylase, protease, lipase, cellulase, and phosphatase, *Lactobacillus* sp. producing lactic acid, and photosynthetic bacteria preventing stink by way of using the stink-causing substances (such as ammonia, hydrogen sulfide, and amines) remaining in the feces of livestock in metabolic process. Recently, probiotics have been reported to have various health function improvement effects including improvement of intestinal health, and thereby spotlighted as major therapeutic substances which can replace existing compound-based therapeutic agents.

Meanwhile, allergy is a biochemical phenomenon that exhibits a unique, altered response to a foreign substance (antigen, allergen). The foreign substance which causes symptoms is called allergen, while the diseases from those symptoms are called allergic diseases. Allergy is a pathological process in the living body resulting from the antigen-antibody reaction. In general, there are four types of allergies depending on the period to trigger the reaction and the complement involvement. Type 1, among those, is anaphylactic type (immediate type) in which target organs are mostly digestive organs, skin and lungs, and the common symptoms include gastrointestinal allergy, urticaria, atrophodermatitis, allergic rhinitis, and bronchial asthma, etc. The pathological mechanism of Type 1 is known as follows: when antigens contact IgE antibodies attached to the surface of mast cells and basophilic leukocytes, the target cells are activated to secrete chemical transmitters such as histamine, leukotriene, and PAF, and then blood vessels and smooth muscles are contracted. Such mechanism can be often combined with Type 4 (delayed type). In other words, such anaphylaxis and allergic reaction can arise due to a variety of changes in the mast cells, etc. The activation of mast cells, which leads to degranulation, is caused by binding of antigen, anti-IgE, lectin, etc. to Fc receptors, stimulation of anaphylatoxin, etc., or other drugs such as calcium ionophore, compound 48/80, codeine and synthetic adrenocorticotropic hormone.

Mast cells and basophil leukocytes in blood are known as main cells in the body to cause many allergic diseases such as allergic rhinitis, allergic dermatitis, asthma, food allergy and anaphylactic shock. These cells have receptors (FcRI) on their surfaces for IgE, which is an antibody causing allergy, and the cells are stimulated by the allergy-causing substances (antigen, allergen) to secrete their own various allergy-causing substances out of the cells (Kim K et al, Eur J Pharmacol, 581:191-203, 2008).

Among allergic diseases, atopic dermatitis, as widely known to the public, is a chronic recurrent skin disease that affects newborns or children and may persist until adulthood. Like asthma or allergic rhinitis, atopic dermatitis is an inflammatory skin disease associated with local infiltration of T-lymphocyte which produces IL-4 and IL-5. IL-4, as well known to the public, controls the development of the T helper 2 (Th2) phenotype, resulting in overproduction of immunoglobulins (Ig) and eosinophilia, and increase of serum IgE levels. 80-90% of the subjects who were positive to the skin test regarding food and inhalant allergens were found to have atopic dermatitis.

There are different treatments for treating or preventing allergic diseases and atopic dermatitis, but no effective treatment has been found yet. Some drug-based treatments are known, but even a short term administration of the drug for the treatment would develop a tolerance and a long-term administration may cause serious side effects, and thus such drug-based treatments of allergic diseases and atopic dermatitis have been avoided recently. Under the circumstances, without treatment having any absolute, obvious effect, irritating symptoms such as itching and redness of skin in addition to allergy often fail to improve.

Under the circumstances, the present inventors devoted themselves to studies of probiotics to find a way to replace drug-based treatments for allergic diseases, including atopic dermatitis, which have no satisfactory treatments. And therefore, the present invention was completed by confirming that a novel strain of *Lactobacillus crispatus* showed excellent therapeutic effects on allergic diseases such as atopic dermatitis, and further confirming that said strain also showed superior effects on anti-inflammation, immunoregulation and anti-fungal activities.

SUMMARY

The purpose of the present invention is to provide a novel strain showing excellent effects on alleviation of allergic symptoms such as atopic dermatitis, alleviation of inflammatory symptoms, and immunoregulation, and a variety of uses thereof.

In order to achieve the purpose, the present invention provides *Lactobacillus crispatus* KBL693 strain (Accession No. KCTC 13519BP).

Also, the present invention provides a food composition or food additive composition comprising at least one selected from the group consisting of said strain, cultures of said strain, lysates of said strain, and extracts of said strain.

The present invention also provides a feed composition or feed additive composition comprising at least one selected from the group consisting of said strain, cultures of said strain, lysates of said strain, and extracts of said strain.

The present invention also provides an anti-fungal composition, such as an anti-dandruff composition, comprising at least one selected from the group consisting of said strain, cultures of said strain, lysates of said strain, and extracts of said strain.

The present invention also provides a pharmaceutical composition for the treatment of allergic diseases such as atopic dermatitis, and/or inflammatory or autoimmune diseases, comprising at least one selected from the group consisting of said strain, cultures of said strain, lysates of said strain, and extracts of said strain.

The present invention also provides a method for treating allergic diseases including atopic dermatitis, and/or inflammatory or autoimmune diseases, comprising administering at least one selected from the group consisting of said strain, cultures of said strain, lysates of said strain, and extracts of said strain to a subject in need thereof.

The present invention also provides a composition comprising at least one selected from the group consisting of said strain, cultures of said strain, lysates of said strain, and extracts of said strain, for the use of preventing or treating allergic diseases including atopic dermatitis, and/or inflammatory or autoimmune diseases.

The present invention also provides the use of a composition for preparing a preventive or therapeutic drug for allergic diseases including atopic dermatitis, and/or inflammatory or autoimmune diseases, comprising at least one selected from the group consisting of said strain, cultures of said strain, lysates of said strain, and extracts of said strain.

The present invention also provides a cosmetic composition comprising at least one selected from the group consisting of said strain, cultures of said strain, lysates of said strain, and extracts of said strain.

The present invention also provides a cosmetic patch or a medical patch comprising at least one selected from the group consisting of said strain, cultures of said strain, lysates of said strain, and extracts of said strain.

BRIEF DESCRIPTION OF DRAWINGS

FIGS. 13A-D. FIG. 13A depicts the experiment plan using mouse models with ovalbumin (OVA)-induced asthma, and FIGS. 13B-D illustrates the observation of lung tissues collected from each group of the normal control group (Control-PBS), asthma-induced control group (OVA-PBS), and test group (OVA-LC206) by an optical microscope after H&E staining.

FIGS. 14A-14D illustrate the determination result of the expression level of total IL-5 and total IL-13 in the lung tissues collected from each of the normal control group (Control-PBS), asthma-induced control group (OVA-PBS), and test group (OVA-KBL693).

BEST MODE

Figure 1:
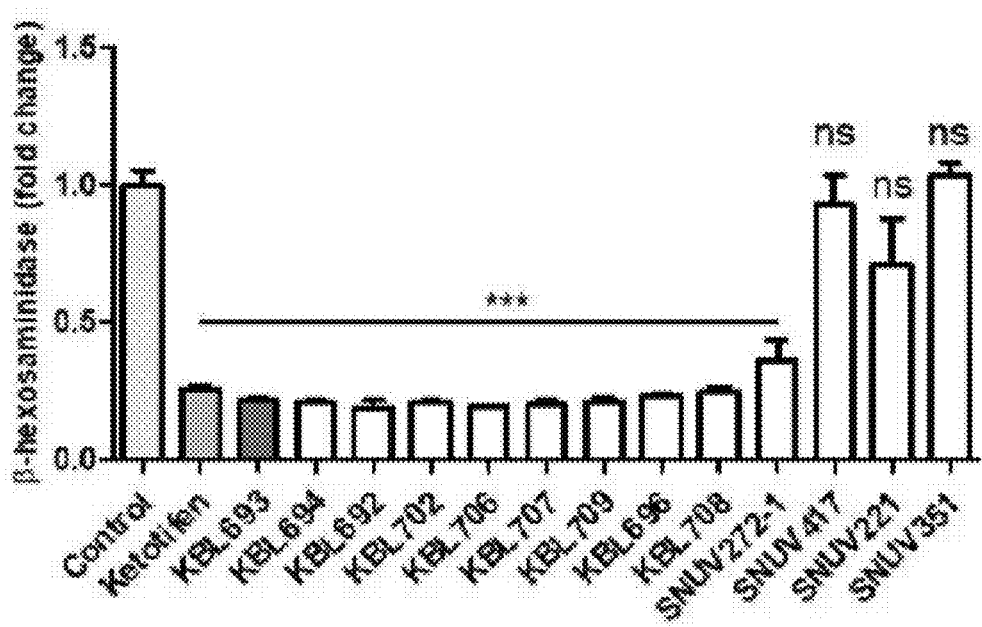
FIG. 1 illustrates the result of comparing the inhibitory effect of histamine secretion by the treatment of various Lactobacillus strains including Lactobacillus crispatus KBL693 strain, and an antihistaminic agent ketotifen, after inducing histamine production by antigen-antibody reaction in RBL 2H3 cell lines.

Unless defined otherwise, all of the technical, scientific terms used in the present specification mean the same as understood by a person having ordinary skills in the art ("those skilled in the art"). In general, the nomenclature used in the present specification is well known in the art and commonly used.

The present invention has found an anti-allergic effect of microorganisms derived from the human body, and selected Lactobacillus crispatus KBL693 strain (Accession No. KCTC 13519BP) having excellent allergy inhibitory effects. Analysis of 16S rDNA of said strain demonstrates that said strain is a novel strain which has never been known to the public.

According to one embodiment of the present invention, the present invention relates to a novel probiotic strain of

*Lactobacillus crispatus* KBL693 (Accession No. KCTC 13519BP), and said strain is characterized by comprising 16S rDNA sequence of SEQ ID NO: 1.

```
16S rDNA sequence of Lactobacillus crispatus
KBL693 strain (Accession No. KCTC 13519BP)
                                  <SEQ ID NO: 1>
CGCGGGGTGGCGCGAGCTATAATGCAGTCGAGCGAGCGGAACTAACAGAT

TTACTTCGGTAATGACGTTAGGAAAGCGAGCGGCGGATGGGTGAGTAACA

CGTGGGGAACCTGCCCCATAGTCTGGGATACCACTTGGAAACAGGTGCTA

ATACCGGATAAGAAAGCAGATCGCATGATCAGCTTTTAAAAGGCGGCGTA

AGCTGTCGCTATGGGATGGCCCCGCGGTGCATTAGCTAGTTGGTAAGGTA

AAGGCTTACCAAGGCGATGATGCATAGCCGAGTTGAGAGACTGATCGGCC

ACATTGGGACTGAGACACGGCCCAAACTCCTACGGGAGGCAGCAGTAGGG

AATCTTCCACAATGGACGCAAGTCTGATGGAGCAACGCCGCGTGAGTGAA

GAAGGTTTTCGGATCGTAAAGCTCTGTTGTTGGTGAAGAAGGATAGAGGT

AGTAACTGGCCTTTATTTGACGGTAATCAACCAGAAAGTCACGGCTAACT

ACGTGCCAGCAGCCGCGGTAATACGTAGGTGGCAAGCGTTGTCCGGATTT

ATTGGGCGTAAAGCGAGCGCAGGCGGAAGAATAAGTCTGATGTGAAAGCC

CTCGGCTTAACCGAGGAACTGCATCGGAAACTGTTTTTCTTGAGTGCAGA

AGAGGAGAGTGGAACTCCATGTGTAGCGGTGGAATGCGTAGATATATGGA

AGAACACCAGTGGCGAAGGCGGCTCTCTGGTCTGCAACTGACGCTGAGGC

TCGAAAGCATGGGTAGCGAACAGGATTAGATACCCTGGTAGTCCATGCCG

TAAACGATGAGTGCTAAGTGTTGGGAGGTTTCCGCCTCTCAGTGCTGCAG

CTAACGCATTAAGCACTCCGCCTGGGGAGTACGACCGCAAGGTTGAAACT

CAAAGGAATTGACGGGGGCCCGCACAAGCGGTGGAGCATGTGGTTTAATT

CGAAGCAACGCGAAGAACCTTACCAGGTCTTGACATCTAGTGCCATTTGT

AGAGATACAAAGTTCCCTTCGGGGACGCTAAGACAGGTGGTGCATGGCTG

TCGTCAGCTCGTGTCGTGAGATGTTGGGTTAAGTCCCGCAACGAGCGCAA

CCCTTGTTATTAGTTGCCAGCATTAAGTTGGGCACTCTAATGAGACTGCC

GGTGACAAACCGGAGGAAGGTGGGGATGACGTCAAGTCATCATGCCCCTT

ATGACCTGGGCTACACACGTGCTACAATGGGCAGTACAACGAGAAGCGAG

CCTGCGAAGGCAAGCGAATCTCTGAAAGCTGTTCTCAGTTCGGACTGCAG

TCTGCAACTCGACTGCACGAAGCTGGAATCGCTAGTAATCGCGGATCAGC

ACGCCGCGGTGAATACGTTCCCGGGCCTTGTACACACCGCCCGTCACACC

ATGGGAGTCTGCAATGCCCAAAGCCGGTGGCCTAACCTTCGGAAGGAGCC

GTCTAAGTAGACAATGTGCA
```

Then, the present inventors conducted experiments regarding the efficacy of said strain, and thereby verified that said strain has an excellent inhibitory effect on allergies such as atopic dermatitis, has immunoregulatory properties, alleviates the inflammatory reaction, and has an anti-fungal activity. Further, the inventors confirmed that said effects could be provided not only in the condition of living bacteria but also under the low temperature sterilization or the high temperature sterilization.

Accordingly, in another embodiment of the present invention, the present invention relates to a food composition or food additive composition comprising at least one selected from the group consisting of *Lactobacillus crispatus* KBL693 strain (Accession No. KCTC 13519BP), cellular component of said strain, cultures of said strain, lysates of said strain, and extracts of said strain.

The composition can be characterized in that it is a health functional food composition having at least one effect selected from the group consisting of alleviation of allergic symptoms such as atopic dermatitis, alleviation of inflammatory symptoms, and immunoregulation.

Said food composition or food additive composition can be readily utilized as the food effective for alleviation of allergic symptoms such as atopic dermatitis, alleviation of inflammatory symptoms, and/or immunoregulation, and for the prevention thereof, for example, as main ingredients or minor ingredients of food, food additives, health functional food composition or functional beverages, but not limited thereto.

The term "food composition" refers to a natural or artificial product comprising at least one nutrient, and more preferably, refers to a product which became edible through certain processing, usually encompassing all of food, food additives, health functional food and functional beverages.

The food that may comprise the said food composition according to the present invention as an additive may include, for example, different types of food, beverages, chewing gum, tea, vitamin complex, or functional food. In addition, the food of the present invention includes special nutritional food (e.g., modified milk, infant/baby food), processed meat products, fish meat products, tofu, muk, noodles (e.g., ramen, Asian noodles), bakery products, health supplement food, seasoning products (e.g., soy sauce, soybean paste, red pepper paste, mixed paste), sauces, confectionery (e.g., snack foods), candies, chocolates, chewing gums, ice-creams, milk products (e.g., fermented milk, cheese), other processed food, Kim-chi, salted food (e.g., different types of Kim-chi, pickled food), beverages (e.g., fruit juice, vegetable juice, soy milk, fermented beverages), and natural seasonings (e.g., broth powder for ramen), but not limited thereto. Said food, beverages or food additives can be prepared in conventional manners.

The term "health functional food" is a group of food to which value is added so as for the function thereof to be exerted and expressed for the predetermined purpose by using physical, biochemical or bioengineering techniques thereto, or a processed food designed so as for the in-vivo adjustment functions of the relevant food composition such as rhythm adjustment in prophylaxis, prevention of disease and recovery from disease to be sufficiently expressed. Such functional food may comprise food supplement additives which are food-scientifically acceptable, and may additionally comprise suitable carriers, excipients and diluents, which are commonly used in the manufacturing thereof.

The term "functional beverages", as used in the present invention, collectively refer to the drink products to relieve thirst or to enjoy the taste. There is no particular limitation thereto, except that, as essential ingredients of the indicated ratio, a composition for alleviation of allergic symptoms such as atopic dermatitis, alleviation of inflammatory symptoms, and/or immunoregulation and the prevention thereof should be comprised in the beverages, and various flavoring agents or natural carbohydrates may be contained therein as additional ingredients like in common beverages.

In addition to the above, the food comprising the food composition or the food additive composition according to the present invention may contain various nutrients, vitamins, minerals (electrolyte), flavoring agents such as synthetic flavoring agents and natural flavoring agents, coloring agents and fillers (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages and the like, and each of the above ingredients may be used alone or in combination with each other.

In the food comprising the food composition according to the present invention, the composition of the present invention may be comprised in an amount of 0.001% by weight to 100% by weight, and preferably 1% by weight to 99% by weight, based on the total weight of the food; in the case of beverages, it may be comprised at an amount of 0.001 g to 10 g, and preferably 0.01 g to 1 g, based on 100 ml. For long-term intake for the purpose of health and hygiene or for the purpose of health control, however, the amount may be below the above-mentioned range; and since the effective ingredients have no problem in terms of safety profile, they can be used at an amount above the range and they are not limited to the amount range mentioned above.

The food composition according to the present invention may comprise Lactobacillus crispatus KBL693 strain alone or in combination with the acceptable carrier, or may be prepared in the form of the composition suitable for consumption by human or animals. That is, the composition may be added to the food which comprises no probiotic bacteria or a couple of probiotic bacteria. For example, the microorganisms which can be used in combination with the strain according to the present invention in preparing the food of the present invention should be suitable for the consumption by human or animals, and have probiotic activities to inhibit pathogenic, harmful bacteria or to improve the balance of microorganisms in the mammalian intestinal tract, upon intake, but not limited thereto. Such probiotic microorganisms may include, for example, yeast such as Saccharomyces, Candida, Pichia or Torulopsis, fungi such as Aspergillus, Rhizopus, Mucor, or Penicillium, and bacteria belonging to the genus of Lactobacillus, Bifidobacterium, Leuconostoc, Lactococcus, Bacillus, Streptococcus, Propionibacterium, Enterococcus, or Pediococcus. Suitable probiotic microorganisms specifically may include, for example, Saccharomyces cerevisiae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus reuteri, Lactobacillus sakei, Lactococcus lactis, or Pediococcus acidilactici. Preferably, the food composition according to the present invention may further comprise a probiotic microorganism mixture having excellent probiotic activities and superior activities of anti-allergy, anti-inflammation and/or immunoregulation to further enhance the effects thereof. The carriers that can be included in the food composition of the present invention may include, for example, extenders, high fiber additives, encapsulating agents, and lipids, which are widely well known in the art. The strain of Lactobacillus crispatus KBL693 in the present invention may be in the lyophilized or encapsulated form or in the form of culture suspensions or dry powders.

The composition of the present invention can also be provided in the form of a feed additive comprising said strain or a feed comprising the same.

The feed additive of the present invention may be in the form of dry or liquid formulation, and further comprise other non-pathogenic microorganisms in addition to the said Lactobacillus crispatus KBL693 strain. The microorganisms that can be added to the feed additive may include, for example, Bacillus subtilis that can produce protease, lipase and sugar-converting enzymes, Lactobacillus strain having a physiological activity and degradability of organic compounds under anaerobic conditions such as in the stomach of cow, filamentous fungi such as Aspergillus oryzae showing effects on increasing weight of animals, milk yield, and digestibility of the feed (Slyter, L. L. J. Animal Sci. 1976, 43. 910-926) and yeast such as Saccharomyces cerevisiae (Johnson, D. E et al. J. Anim. Sci., 1983, 56, 735-739; Williams, P. E. V. et al, 1990, 211).

The feed additive of the present invention may additionally comprise at least one enzyme agent in addition to said Lactobacillus crispatus KBL693 strain. The additional enzyme agents can be in a dry or liquid form, and may include, for example, steatolytic enzymes such as lipase, phytase to produce phosphate and inositol phosphate by degrading phytic acid, amylase, i.e., an enzyme to hydrolyze α-1,4-glycoside bond included in, for example, starch and glycogen, phosphatase, i.e., an enzyme to hydrolyze organic phosphoric acid ester, carboxymethylcellulase to degrade cellulose, xylase to degrade xylose, maltase to hydrolyze maltose into two glucose molecules, and sugar producing enzymes such as invertase to produce glucose-fructose mixture by hydrolyzing saccharose.

In the use of Lactobacillus crispatus KBL693 strain of the present invention as feed additives, the raw ingredients for the feed, such as peanuts, peas, beets, pulp, grain by-products, animal guts powder and fish meal powder, including various grains and soybean protein, can be used. They may be processed or not, and can be used without limitation. The processing may include, but not limited thereto, such a process that the raw ingredients of the feed are charged and can be compressed under pressure against a given outlet, and for proteins, extrusion by which proteins are degenerated to increase availability may be preferably used. Extrusion denatures proteins through thermal treatment to destroy antienzyme factors, which is advantageous. Further, for soybean proteins, the digestibility thereof can be improved through extrusion to inactivate anti-nutrients such as a trypsin inhibitor, one of inhibitors of protease that are present in soybeans. Further, extrusion can promote improvement of digestibility by protease, enhancing the nutritional value of soybean proteins.

According to another embodiment of the present invention, the present invention relates to an anti-fungal composition comprising at least one selected from the group consisting of said strain, cultures of said strain, lysates of said strain, and extracts of said strain.

The composition can be characterized by showing an anti-fungal activity on the one selected from the group consisting of Malassezia furfur, Malassezia globosa and Malassezia restricta, but not limited thereto.

The composition can be a composition for preventing, alleviating or treating seborrheic dermatitis or dandruff, and said seborrheic dermatitis can be on scalp.

Further, said composition can be a composition for preventing, alleviating or treating urticaria, rash, tinea corporis, tinea cruris, or tinea pedis, due to mycotic infection.

Said strain, and cultures of said strain, lysates of said strain, and extracts of said strain can be comprised in an amount of 0.1% by weight to 50% by weight, based on the total weight of the composition.

Said anti-fungal composition may be a pharmaceutical composition, a cosmetic composition or a health food composition, and it can also be a skin external preparation.

Said cosmetic composition can be provided in all dosage forms which are suitable for topical application, for example, in the form of liquid, oil-in-water type emulsion, water-in-oil type emulsion, suspension, solid, gel, powder, paste, foam or aerosol. Said compositions of the above dosage forms can be prepared in conventional methods used in the art.

In addition to the above ingredients, said composition may comprise other ingredients at an amount which does not harm the main effect, preferably, at an amount to provide a synergistic effect on the main effect. The composition according to the present invention may comprise a substance selected from the group consisting of vitamins, polypeptides, polysaccharides, and sphingolipid. Further, the cosmetic composition of the present invention may comprise a moisturizer, an emollient agent, a surfactant, a UV absorbent, a preservative, a sterilizer, an antioxidant, a pH adjusting agent, organic and inorganic pigments, flavoring agent, a cooling agent or an antiperspirant agent. The combination percentage of said ingredients can be selected by those skilled in the art within the range not to hinder the purpose and effect of the present invention, and can be in a range from 0.01% by weight to 5% by weight, and specifically from 0.01% by weight to 3% by weight, based on the total weight of the composition.

According to the above embodiment, the anti-fungal composition of the present invention can be a skin external preparation such as cream, ointment, shampoo, or treatment.

According to another embodiment of the present invention, the present invention relates to a pharmaceutical composition for the treatment or prevention of allergic diseases including atopic dermatitis, and/or inflammatory or autoimmune diseases, comprising at least one selected from the group consisting of cellular component of *Lactobacillus crispatus* KBL693 strain, cultures of said strain, lysates of said strain, and extracts of said strain.

The pharmaceutical composition of the present invention can be provided in a form of cellular component of live bacteria, dry strain, cultures of said strain, lysates of said strain, or a composition in combination with a pharmaceutically acceptable carrier or media. The carriers or media that can be used herein may include solvent, a dispersant, a coating, an enhancer, a controlled-release formulation (i.e., sustained-release formulation), or at least one inert excipient including starch, polyol, granules, microtine cellulose, microcrystalline cellulose such as Celphere, Celphere beads, diluent, lubricant, binder, disintegrant. The tablet of the above composition may be, if desired, coated by a standard aqueous or non-aqueous technique. The examples of the pharmaceutically acceptable carrier and the excipient for the use as the pharmaceutically acceptable inert carrier, and said additional ingredients may include, for example, a binder, a filler, a disintegrant, a lubricant, an antimicrobial agent and a coating agent, but not limited thereto.

Further, the pharmaceutical composition of the present invention can be used as an external preparation comprising a dosage form selected from the group consisting of ointments, creams, pastes, liquids and solutions for cutaneous application, glycerogelatins, liniments, powders for cutaneous application, aerosols, and plasters.

In the present invention, said allergic diseases refer to the conditions associated with IL-4 or IL-5 expressions, and may include, for example, eczema, allergic asthma, atopic dermatitis, allergic rhinitis, allergic conjunctivitis, urticaria, or anaphylaxis. Preferably, the present invention may be characterized in that the diseases are selected from the group consisting of infant eczema, allergic asthma, allergic rhinitis, atopic dermatitis, allergic conjunctivitis, and food allergy, but not limited thereto.

In the present invention, said inflammatory or autoimmune diseases, or the symptoms which can be alleviated by immunoregulation are those that can be treated, alleviated or prevented by promoting the expression or secretion of IL-10 which is an anti-inflammatory, immunoregulatory cytokine, and may include, for example, rheumatoid arthritis, rheumatic fever, lupus, systemic scleroderma, atopic dermatitis, psoriasis, psoriatic arthritis, asthma, Guilian-Barre syndrome, myasthenia gravis, dermatomyositis, polymyositis, multiple sclerosis, autoimmune encephalomyelitis, polyarteritis nodosa, Hashimoto's thyroiditis, temporal arteritis, juvenile diabetes, alopecia areata, pemphigus, aphthous stomatitis, autoimmune hemolytic anemia, Wegener's granulomatosis, Sjogren's syndrome, Addison's disease, Crohn's disease, Behcet's disease, edema, conjunctivitis, periodontitis, rhinitis, otitis media, chronic sinusitis, pharyngolaryngitis, tonsillitis, bronchitis, pneumonia, gastric ulcer, gastritis, colitis, gout, eczema, acne, contact dermatitis, seborrheic dermatitis, ankylosing spondylitis, fibromyalgia, osteoarthritis, peri-arthritis of the shoulder, tendinitis, tenosynovitis myositis, hepatitis, cystitis, nephritis, sepsis, vasculitis, bursitis and the like, but not limited thereto.

The term 'treating', unless mentioned otherwise, refers to reversing or alleviating the diseases or conditions used with said term or one or more symptoms thereof, inhibiting the progression of the same or preventing the same. The term 'treatment' as used in the present invention refers to an act of 'treating' as defined above. Accordingly, treatment or therapeutic regimen of a disease in mammals may include one or more of the following:

(1) Inhibit the growth of the disease, that is, inhibit its development
(2) Prevent the spread of the disease
(3) Alleviate the disease
(4) Prevent recurrence of the disease, and
(5) Palliate the symptoms of the disease A composition of the present invention for preventing or treating allergic diseases such as atopic dermatitis, and/or inflammatory or autoimmune diseases may comprise a pharmaceutically effective amount of *Lactobacillus crispatus* KBL693 strain alone or in combination of with at least one of pharmaceutically acceptable carriers, excipients or diluents.

In the present invention, the term "effective amount" means an amount that is high enough to provide a desired effect but is low enough to prevent serious side effects under medical judgment. The amount of microorganisms administered to the body by the composition of the present invention can be appropriately adjusted in consideration of the administration route and the administration target.

The composition of the present invention can be administered to a subject once or more per day. Unit dosage means physically discrete units suitable for unit administration to human subjects and other mammals, and each unit comprises a suitable pharmaceutical carrier and a predetermined amount of *Lactobacillus crispatus* KBL693 strain of the present invention to provide a therapeutic effect. The dosage unit for oral administration to an adult patient preferably contains 0.001 g or more of the microorganism of the present invention, and the oral dosage of the composition of the present invention is from 0.001 g to 10 g, and preferably from 0.01 g to 5 g per dose. The pharmaceutically effective amount of the microorganism of the present invention is from 0.01 g to 10 g/day. However, the dosage varies depending on the severity of the patient's disease and the microorganisms and auxiliary effective ingredients used together. In addition, the total daily dosage can be divided into several times and continuously administered as needed. Accordingly, the above dosage ranges do not limit the scope of the present invention in any way.

Further, the term "pharmaceutically acceptable" as used above refers to a composition that is physiologically acceptable and does not cause an allergic reaction such as gastrointestinal disorder, or dizziness, or similar reaction when administered to a human.

A composition of the present invention can be formulated using methods known in the art so that rapid, sustained or delayed release of the active ingredients, after administered to a mammal, can be provided. The dosage forms may be powders, granules, tablets, emulsions, syrups, aerosols, soft or hard gelatin capsules, sterile injection solutions, or sterile powders. Further, the composition of the present invention for preventing or treating allergic diseases such as atopic dermatitis, and/or inflammatory or autoimmune diseases can be administered via several routes, including oral, transdermal, subcutaneous, intravenous or intramuscular administration. The dosage of the active ingredients can be appropriately selected depending on various factors such as the route of administration, the patient's age, sex, weight, and the severity of the patient. The composition of the present invention for treating allergic diseases such as atopic dermatitis, and/or inflammatory or autoimmune diseases can be administered in combination with a known compound having the effect of preventing, alleviating or treating the relevant symptoms.

The pharmaceutical composition of the present invention, in particular, can be provided in an oral unit dosage form of an enteric coated formulation. The term "enteric coating", as used herein, comprises any known pharmaceutically acceptable coating which can remain in the stomach without degrading by the gastric acid and can sufficiently disintegrate in the intestinal tract to release active ingredients therein. The "enteric coating" of the present invention refers to a coating that can be maintained for 2 hours or more when an artificial gastric juice such as an HCl solution of pH 1 is contacted thereto at 36° C. to 38° C., and subsequently can degrade, preferably in an artificial intestinal juice such as a $KH_2PO_4$ buffer solution of pH 6.8 in 30 minutes.

The enteric coating of the present invention is coated on one core in an amount of from about 16 mg to 30 mg, preferably from 16 mg to 20 mg or 25 mg or less. When the thickness of the enteric coating of the present invention is 5 μm to 100 μm, and preferably 20 μm to 80 μm, satisfactory results can be obtained as an enteric coating. The material of the enteric coating can be suitably selected from known polymeric materials. Suitable polymeric materials are listed in a number of known documents (L. Lachman et al., The Theory and Practice of Industrial Pharmacy, $3^{rd}$ ed., 1986, pp. 365-373; H. Sucker et al., Pharmazeutische Technologie, Thieme, 1991, pp. 355-359; Hagers Handbuchder pharmazeutischen Praxis, 4th ed., Vol. 7, pp. 739-742, and 766-778, (SpringerVerlag, 1971); and Remington's Pharmaceutical Sciences, 13th ed., pp. 1689-1691 (Mack Publ., Co., 1970)), and cellulose ester derivatives, cellulose ethers, a copolymer of acrylic resin and methylacrylate, and a copolymer of maleic acid and phthalic acid derivatives can be included therein.

The enteric coating of the present invention can be prepared using a conventional enteric coating method in which an enteric coating solution is sprayed onto a core. Suitable solvents used for the enteric coating process are alcohols such as ethanol, ketones such as acetone, halogenated hydrocarbon solvents such as dichloromethane ($CH_2Cl_2$), and mixed solvents of these solvents. A softener such as di-n-butyl phthalate or triacetin is added to the coating solution in a ratio of 1:about 0.05 to about 0.3 (coating material:softener). It is appropriate to carry out the spraying process continuously, and it is possible to adjust the spraying amount in consideration of the conditions of coating. The spraying pressure can be variously adjusted, and satisfactory results can be obtained generally with a spraying pressure of about 1 bar to about 1.5 bar.

In another embodiment of the present invention, the present invention provides the use of said strain or said composition for preventing or treating allergic diseases such as atopic dermatitis, and/or inflammatory or autoimmune diseases, and the use of said strain or said composition for preparing a therapeutic agent for the above diseases.

Specifically, the present invention relates to a composition comprising at least one selected from the group consisting of said strain, cultures of said strain, lysates of said strain, and extracts of said strain, for the use of preventing or treating allergic diseases including atopic dermatitis, and/or inflammatory or autoimmune diseases.

The present invention also relates to the use of a composition for preparing a preventive or therapeutic drug for allergic diseases including atopic dermatitis, and/or inflammatory or autoimmune diseases, comprising at least one selected from the group consisting of said strain, cultures of said strain, lysates of said strain, and extracts of said strain.

The term 'prevention', as used herein, is associated with averting, delaying, impeding or hindering diseases to reduce the same.

The term 'treatment', as used herein, is associated with caring for a subject suffering from diseases in order to ameliorate, cure or reduce the symptoms of the diseases or to reduce or stop the progression of the diseases.

In another embodiment of the present invention, the present invention provides a method for preventing or treating allergic diseases including atopic dermatitis, and/or inflammatory or autoimmune diseases, comprising administering a pharmaceutically effective amount of the strain or said composition to a subject in need of prevention or treatment of said diseases, or in need of alleviation of said diseases.

Specifically, the present invention provides a method for treating allergic diseases including atopic dermatitis, and/or inflammatory or autoimmune diseases, comprising administering a therapeutically effective amount of at least one selected from the group consisting of said strain, cultures of said strain, lysates of said strain, and extracts of said strain to a subject in need thereof.

Since the pharmaceutical composition used for the method for preventing or treating said diseases, and the administration method thereof have been described above, the overlapping contents between the composition and the method will be omitted herein to avoid excessive complexity of the present specification.

Meanwhile, the said subject to which the composition for preventing or treating said diseases can be administered includes all animals including human. For example, the subject may be an animal such as dog, cat, or mouse.

In another embodiment of the present invention, the present invention relates to a cosmetic composition comprising a pharmaceutically effective amount of at least one selected from the group consisting of the cellular component of *Lactobacillus crispatus* KBL693 strain, cultures of said strain, lysates of said strain, and extracts of said strain.

The cosmetic composition may be characterized by its function of alleviating at least one sensitive skin condition selected from the group consisting of cutaneous allergy, skin urticaria, atopic dermatitis, psoriasis, mycotic infections and eczema, but not limited thereto.

The term 'cosmetic composition', as used herein, refers to a composition comprising at least one selected from the group consisting of the cellular component of *Lactobacillus crispatus* KBL693 strain, cultures of said strain, lysates of said strain, and extracts of said strain, and may take any type of dosage form. For example, the cosmetics prepared by using the said cosmetic composition may include creams, packs, lotions, essences, toners, foundations and makeup bases, and may be commercialized in any dosage forms listed above to achieve the purpose of the present invention, but not limited thereto. The ingredients comprised in the cosmetic composition of the present invention include those commonly used in cosmetic compositions, in addition to the above ingredients, for example, conventional adjuvants such as antioxidants, stabilizers, solubilizers, vitamins, pigments and fragrances, and carriers.

In another embodiment of the present invention, the present invention relates to a functional patch comprising at least one selected from the group consisting of the cellular component of *Lactobacillus crispatus* KBL693 strain, cultures of said strain, lysates of said strain, and extracts of said strain, and said functional patch may be used for cosmetic or medical purpose.

The patch may be characterized by its function of alleviating at least one sensitive skin condition selected from the group consisting of cutaneous allergy, skin urticaria, atopic dermatitis, psoriasis, mycotic infections and eczema, but not limited thereto.

In the present invention, the patch is typically a small adhesive bandage containing the substances to be delivered, and the bandage can take a variety of forms. The simplest form is an adhesive single body comprising a reservoir containing the substances to be delivered placed on a support. The reservoir is typically formed from a cosmetically or pharmaceutically acceptable pressure sensitive adhesive, but in some cases may also be formed from non-adhesive materials provided with a thin adhesive layer suitable for the skin contacting surface. The rate at which the substances to be delivered are administered from the patch to the subject wearing the patch can be changed because the permeability of the skin to the substances to be delivered usually depends on individuals and the location of the skin, which can be easily selected by those skilled in the art.

Hereinafter, the present invention will be described in more detail through examples. These examples are only for illustrating the present invention, and it will be apparent to those skilled in the art that the scope of the present invention is not to be construed as being limited by these examples.

Example 1. Alleviation and Treatment Effects by KBL693 for Allergic Reactions Resulting from Inhibition of Histamine Secretion in Basophils It has been reported that, in an allergic reaction, histamine is expressed in tissues, causing an inflammatory reaction, and suppressing histamine secretion leads to alleviation of allergic symptoms by blocking the reaction by histamine. The present invention attempted to select probiotic strains that can show effects on the alleviation and treatment of allergic reactions through inhibition of histamine secretion. To this end, a total of eight *Lactobacillus* strains derived from human vagina were evaluated for the ability to suppress histamine secretion. The ability to suppress histamine secretion was confirmed by inducing degranulation after culturing the RBL-2H3 cell line and then measuring the activity of β-hexosaminidase co-secreted with histamine, using a colorimetric reaction with a substrate.

1-1. Incubation of RBL-2113 Cell Lines

RBL-2H3 (ATCC NO. CRL-2256) cells were cultured in DMEM medium supplemented with 10% FBS (fetal bovine serum), penicillin (100 μg/mL), and streptomycin (100 μg/mL) at 37° C. under 5% $CO_2$, and then subcultured once every three days. RBL-2H3 cells were seeded onto a 6-well plate with a concentration of $1 \times 10^6$ cells/well, then cultured for 3 hours, and then treated with IgE (0.5 μg/mL) to incubate for 16 to 20 hours.

1-2. Incubation of Strains and Preparation of Culture Solution

The *Lactobacillus crispatus* strains to be used were cultured in MRS medium supplemented with 0.5% cysteine, were activated through a total of two subcultures at 18-hour intervals, and then were used in experiments. The resulting culture solution was centrifuged at 15,000×g for 3 minutes to collect the supernatant.

1-3. Inducing Degranulation after Treatment of Strains

After removing the medium of RBL-2H3 cells which were previously seeded onto a 6-well plate, the cells were washed twice with 1 mL of Siraganian buffer (pH 7.2). Thereafter, the cells were treated with 120 μL of the previously prepared bacterial culture solution or the positive control group ketotifen (20 μg/mL) per well, incubated for 20 minutes in the 5% $CO_2$ incubator at 37° C., followed by treating with 60 μL of antigen (DNP-HAS, 1 μg/mL) to induce degranulation by the antigen-antibody reaction. As a negative control, degranulation was induced after treating with 120 μL of the Siraganian buffer. The reaction was carried out in the 5% $CO_2$ incubator at 37° C. for 20 minutes, and then the supernatant was collected.

1-4. Identification of Color Reaction

To identify the activity of β-hexosaminidase, 25 μL of the supernatant collected in Example 1-3 was transferred to each well of a 96-well plate, and then 25 μL of each substrate (p-nitrophenyl N-acetyl-D-glucosaminidase) was added thereto, and followed by a reaction at 37° C. in the 5% $CO_2$ incubator for 90 minutes. Then, 200 μL of stop solution ($Na_2CO_3/NaHCO_3$) was added to stop the reaction and then absorbance was measured at 405 nm. The absorbance when treated with each type of *Lactobacillus crispatus* was compared to the negative control group and converted to percentage to show the level of inhibition of the degranulation.

As a result, as can be seen in FIG. 1 and Table 1, ten types of *Lactobacillus crispatus* strains including the KBL693 strain showed significantly lower amount of β-hexosaminidase secretion compared to the negative control group, and nine types among them showed the amount of β-hexosaminidase secretion even lower than that of the commercially available antihistamine agent ketotifen, a positive control. As a result, it was found that *Lactobacillus crispatus* strains including the KBL693 strain exhibited excellent degranulation-preventing activity to effectively alleviate allergic symptoms caused by excessive secretion of histamine.

TABLE 1

| Species | Strain under Treatment or Treatment Drug | β-hexosaminidase (fold change) |
|---|---|---|
| (Negative control) | Siraganian buffer | 1.0 |
| (Positive control) | Ketotifen | 0.2569 |
| Lactobacillus crispatus | KBL693 | 0.2140 |
| Lactobacillus crispatus | KBL694 | 0.2063 |
| Lactobacillus crispatus | KBL692 | 0.1904 |
| Lactobacillus crispatus | KBL702 | 0.2065 |
| Lactobacillus crispatus | KBL706 | 0.1943 |
| Lactobacillus crispatus | KBL707 | 0.2008 |
| Lactobacillus crispatus | KBL709 | 0.2128 |
| Lactobacillus crispatus | KBL696 | 0.2331 |
| Lactobacillus crispatus | KBL708 | 0.2464 |
| Lactobacillus crispatus | SNUV272-1 | 0.3632 |
| Lactobacillus fermentum | SNUV417 | 0.9284 |
| Lactobacillus jensenii | SNUV221 | 0.7088 |
| Lactobacillus vaginalis | SNUV351 | 1.0336 |

Example 2. Alleviation and Treatment Effects by KBL693 for Allergic Reactions Resulting from Inhibition of Th2 Type Cytokines in T Cells Type-2 helper T cell (Th2)-related cytokines, such as IL-4 and IL-5, have been reported to contribute to chronic allergic reactions by increasing Th2-related immune reactions and increasing IgE production (Passante E, *Inflamm. Res.* 2009). The present invention attempted to further compare the effects on inhibition of chronic allergic reactions among *Lactobacillus crispatus* strains showing an excellent effect on inhibition of histamine secretion in Example 1. To this end, the effect of inhibiting the secretion of IL-4 and IL-5 was tested as follows, using EL4 cell line which are the mouse T cell line.

2-1. Incubation of EL-4 Cell Lines

EL4 (ATCC NO. TIB-39) cells were cultured in DMEM medium supplemented with 10% FBS, penicillin (100 μg/mL), and streptomycin (100 μg/mL) at 37° C. under 5% $CO_2$, and then subcultured once every three days. EL4 cells were seeded onto a 24-well plate with a concentration of $4 \times 10^5$ cells/well, then cultured for 16 to 20 hours to induce allergic reactions, and treated with strains.

2-2. Incubation of Strains and Recovery

A total of nine *Lactobacillus crispatus* strains including KBL693 to be used (KBL693, KBL709, KBL702, KBL696, KBL708, KBL707, KBL692, KBL694, and KBL706) were cultured in MRS medium supplemented with 0.5% cysteine, were activated through a total of two subcultures at 18-hour intervals, and then were used in experiments. The resulting culture solution was centrifuged at 15,000×g for 3 minutes, and the precipitate was washed with a PBS buffer. The strains were stained for 15 minutes with SYTO9 and PI by using LIVE/DEAD™ BacLight™ Bacterial Viability and Counting Kit for flow cytometry (Thermo Fisher Scientific, USA). Then, the contained beads were added, and the number of stained live bacteria was calculated by using a flow cytometry assay.

2-3. Strain Treatment and Measurement of an Amount of IL-4 and IL-5 Secretion after Inducing Allergic Reactions In order to induce allergic reactions in the EL4 cells previously seeded onto a 24 well plate, each well was treated with 100 μL of PMA (20 ng/mL) and ionomycin (1 μg/mL). Then, 300 μL of the previously prepared strains were treated in the ratio of cell to strain of 1:10. After incubation for 24 hours in the 5% $CO_2$ incubator at 37° C., the supernatant was collected, and Mouse IL-4 ELISA set (Cat NO. 555232, BD OptEIA™) and Mouse IL-5 ELISA set (Cat NO. 555236, BD OptEIA™) were used to measure the amount of IL-4 and IL-5 secreted, according to the manufacturer's method.

Figure 2:
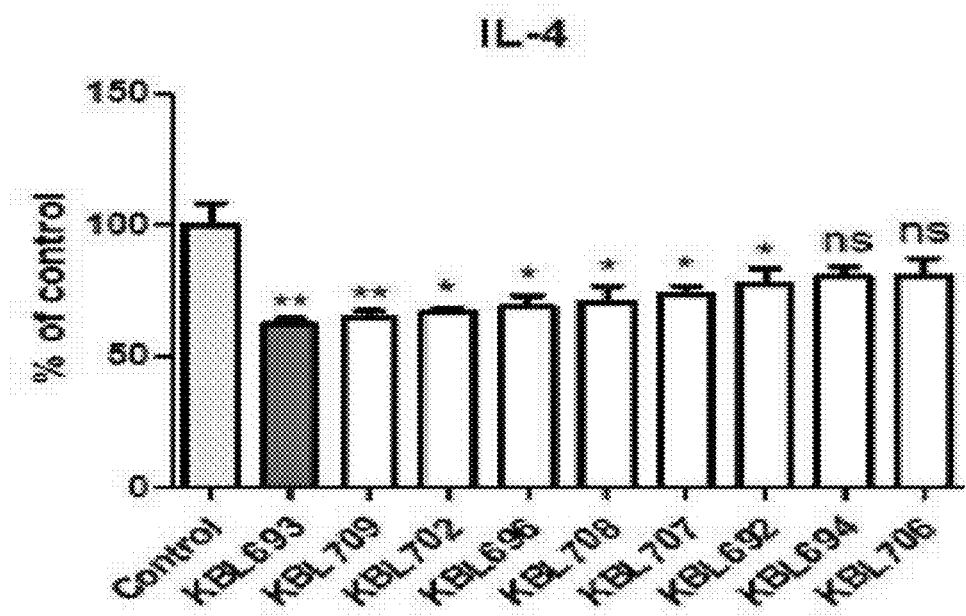
FIG. 2 illustrates the result confirming the inhibitory effect of IL-4 expression by various Lactobacillus strains including Lactobacillus crispatus KBL693 strain, after inducing allergic reaction in EL4 cell lines.
Figure 3:
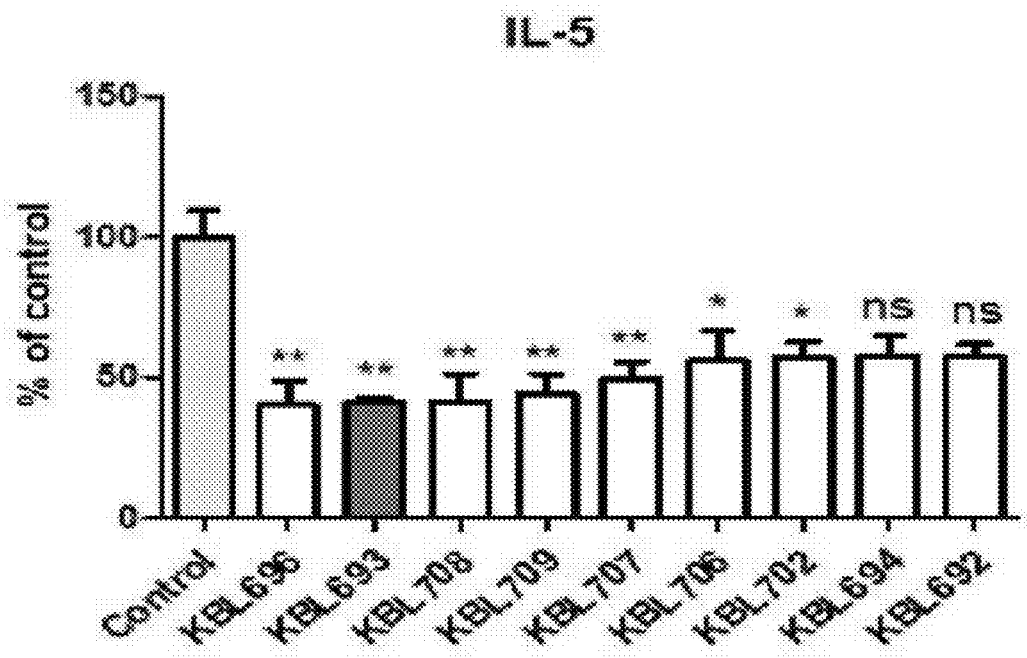
FIG. 3 illustrates the result confirming the inhibitory effect of IL-5 expression by various Lactobacillus strains including Lactobacillus crispatus KBL693 strain, after inducing allergic reaction in EL4 cell lines.

As a result, as shown in FIGS. 2 and 3, those *Lactobacillus crispatus* strains generally showed effects on inhibition of IL-4 and IL-5 secretion, and especially in the strain KBL693, among those, the lowest amount of IL-4 secretion was found, and the second lowest amount of IL-5 secretion was found. Accordingly, it was found that KBL693 could provide therapeutic and preventive effects on allergies through inhibition of secretion of Th2 type cytokines that mediate an allergic reaction.

Example 3. Effects of KBL693 on Alleviation and Treatment of Allergic Reactions Resulting from IgE Inhibition Immunoglobulin E (IgE) is a type of immunoglobulin and is known to be involved in the development of allergic diseases. In general, the total amount of IgE in serum is measured as one of the most prioritized methods for diagnosing an allergic disease. Thus, the present invention attempted to verify the IgE secretion inhibitory effect by KBL693 by using the U266B1 cell line which is human B cell line.

3-1. Incubation of U266B1 Cell Lines

U266B1 (ATCC NO. TIB-196) cells were cultured in RPMI-1640 medium supplemented with 10% FBS, penicillin (100 μg/mL), and streptomycin (100 μg/mL) at 37° C. under 5% $CO_2$, and then subcultured once every three days. The U266B1 cells were seeded onto a 24-well plate with the concentration of $1 \times 10^5$ cells/well, then cultured for 16 to 20 hours to induce inflammatory reactions, and then thereby treated with the strains.

3-2. Incubation of Strains and Recovery

The strains to be used in the present experiment were prepared in a same manner as Example 2-2.

3-3. Strain Treatment and Measurement of the Amount of IgE Secretion after Inducing Allergic Reactions In order to induce allergic reactions in the U266B1 cells previously seeded onto a 24 well plate, each well was treated with 100 μL of LPS (10 μg/mL) and IL-4 (5 ng/mL). Then, 300 μL of the previously prepared strains were treated in the ratio of cell to strain of 1:10. After incubation for 48 hours in the 5% $CO_2$ incubator at 37° C., the supernatant was collected, and Human IgE ELISA kit (Cat NO. E88-108, Bethyl Laboratories) was used to measure, according to the manufacturer's method.

Figure 4:
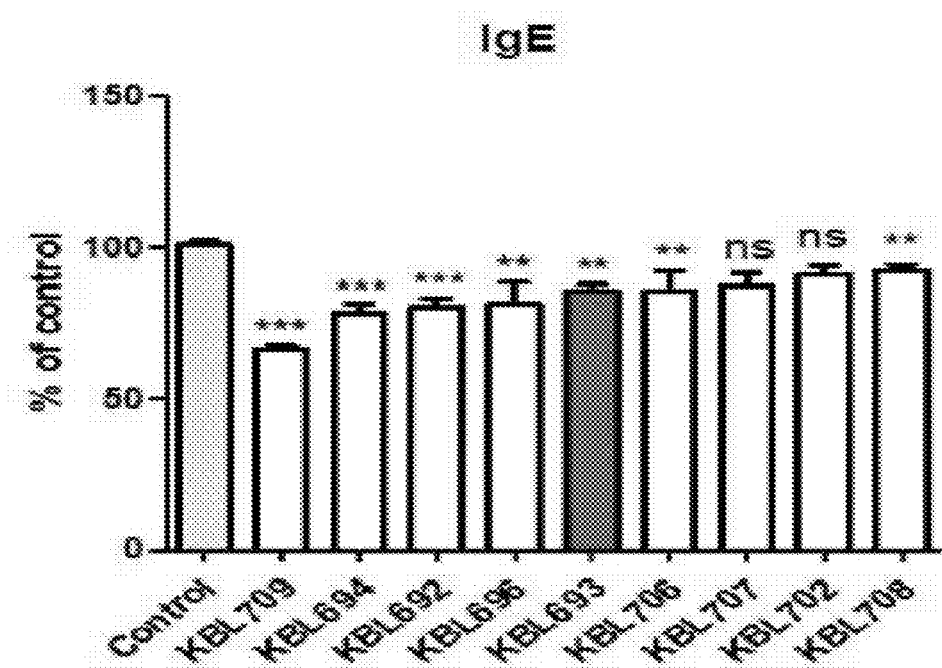
FIG. 4 illustrates the result confirming an inhibitory effect of IgE secretion by various Lactobacillus strains including Lactobacillus crispatus KBL693 strain, after inducing allergic reaction in U266B1 cell lines.

As a result, as shown in FIG. 4, it was confirmed that the groups treated with seven *Lactobacillus crispatus* strains including KBL693 showed effects on inhibition of IgE secretion, compared to the negative control group. The present experiment showed that KBL693 could provide therapeutic and preventive effects on allergic diseases through inhibition of IgE, a major factor involved in allergic reactions.

Example 4. Analysis of Immunoregulatory and Inflammation Inhibitory Effects of KBL693

Immunoregulatory and inflammatory inhibitory effects of KBL693 were also verified in addition to the anti-allergic efficacy thereof. To this end, the ratio between IL-10, a representative cytokine that has an immunoregulatory function, and TNF-α and IL-6, which are cytokines as the major indicators of an inflammatory reaction (IL-10/TNF-α, IL-10/IL-6) was measured by using macrophage, which plays a critical role in the inflammatory reaction.

4-1. Incubation of RAW264.7 Cell Lines

RAW264.7 (ATCC NO. TIB-71) cells were cultured in DMEM medium supplemented with 10% FBS, penicillin (100 μg/mL), and streptomycin (100 μg/mL) at 37° C. under 5% $CO_2$, and then subcultured once every three days. RAW264.7 cells as incubated were seeded onto a 24-well plate with the concentration of $1\times10^5$ cells/well, then cultured for 16 to 20 hours, and then used for Example 4-3.

4-2. Incubation of Strains and Preparation of Samples

The culture solutions were corrected with the same number of live bacteria and then prepared as three samples: live bacteria, pasteurization and heat killing. The samples for live bacteria, pasteurization and heat killing were prepared according to the same method as that of Example 2-2.

Then, the sample for pasteurization was reacted at 70° C. for 30 minutes and prepared through the same centrifugation process. The sample of heat killing was sterilized at 121° C. for 15 minutes and prepared through the same process. As a negative control group, the MRS medium supplemented with 0.5% cysteine was used.

4-3. Strain Treatment and Measurement of an Amount of Inflammatory Cytokines Secreted after Inducing Inflammatory Reactions In order to induce inflammatory reactions in RAW264.7 cells previously seeded onto a 24-well plate, each well was treated with 500 μL of LPS (20 ng/mL). Then, 300 μL of the previously prepared strains were treated in the ratio of cell to strain of 1:10, and incubated for 24 hours in the 5% $CO_2$ incubator at 37° C. The supernatant in the cultured cell-strain mixture was collected and Mouse TNF ELISA Set II (Cat No. 558534, BD OptEIA™), Mouse IL-6 ELISA Set (Cat No. 555240, BD OptEIA™), and Mouse IL-10 ELISA Set (Cat No. 555252, BD OptEIA™) were used to measure an amount of each cytokine, according to the manufacturer's method.

Figure 5:
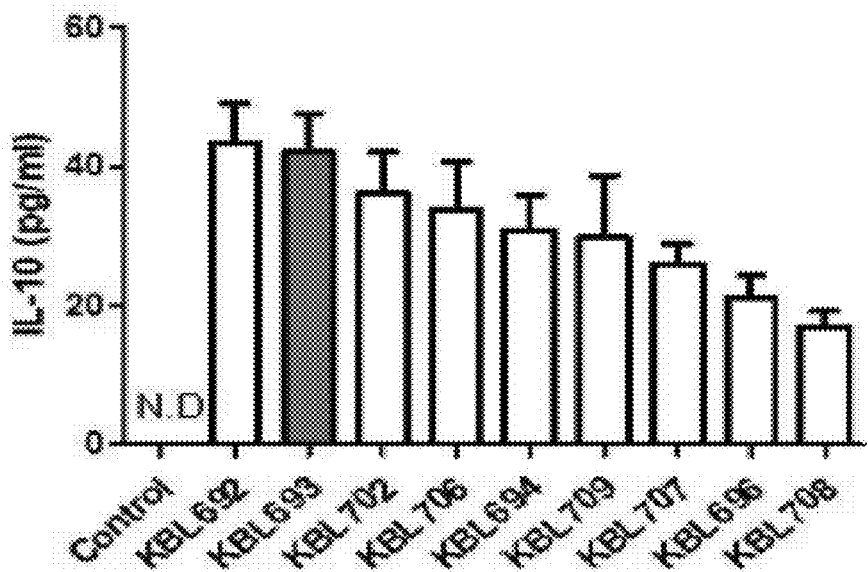
FIG. 5 illustrates the result of observation of the remarkable effect of increasing the amount of anti-inflammatory cytokine IL-10 secretion by the treatment of the KBL693 strain, when treating with various Lactobacillus strains after inducing inflammatory reaction in RAW 264.7 cell lines.
Figure 6:
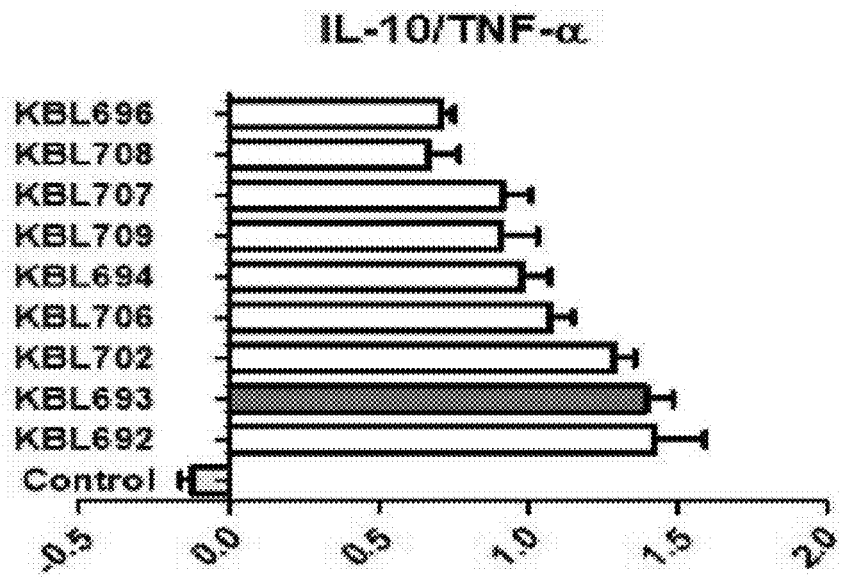
FIG. 6 illustrates the result confirming the remarkable immunoregulatory and anti-inflammatory effect by the treatment of the KBL693 strain with an IL-10/TNF-α value, when treating with various Lactobacillus strains after inducing inflammatory reaction in RAW 264.7 cell lines.
Figure 7:
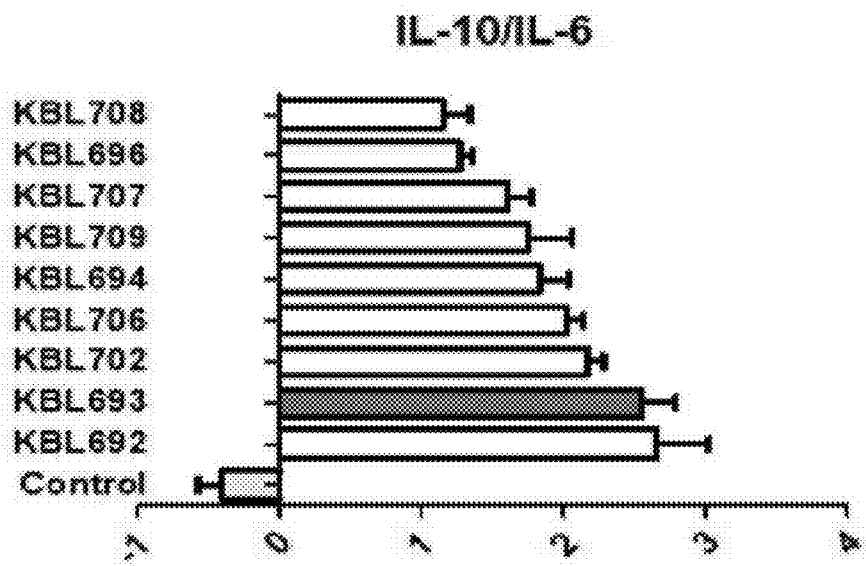
FIG. 7 illustrates the result confirming the remarkable immunoregulatory and anti-inflammatory effect by the treatment of the KBL693 strain with an IL-10/IL-6 value, when treating with various Lactobacillus strains after inducing inflammatory reaction in RAW 264.7 cell lines.

As a result, as shown in FIG. 5, it was confirmed that especially KBL693, among *Lactobacillus crispatus* strains, induced IL-10 secretion and thus showed excellent effects in terms of immunoregulation and inflammatory reaction suppression. As shown in FIGS. 6 and 7, from the ability to secrete IL-10 corrected with the pro-inflammatory cytokines TNF-α and IL-6, it was confirmed that the KBL693 treatment group showed the inflammation inhibitory effect and immunoregulatory ability much enhanced compared to the control group. Accordingly, it has been found that KBL693 has immunoregulatory and inflammation inhibitory activities through IL-10 secretion. In addition, these effects were similarly confirmed not only in live bacteria but also in pasteurized or heat killed dead bodies (see Table 2 and Table 3), indicating that KBL693 can be used to regulate immune and suppress inflammatory reactions in various forms such as dead bacteria.

TABLE 2

| IL-10/TNF-a | Live | Heat-killed | Pasteurized |
| --- | --- | --- | --- |
| Control | −1.7574022 (N.D.) | −1.6268471 (N.D.) | −1.9978721 (N.D.) |
| KBL693 | 4.22079373 | 3.82025311 | 4.97474621 |

N.D.: Not Determined

TABLE 3

| IL-10/IL-6 | Live | Heat-killed | Pasteurized |
| --- | --- | --- | --- |
| Control | −3.5789041 (N.D.) | −4.2268549 (N.D.) | −4.712413 (N.D.) |
| KBL693 | 4.95082596 | 4.9303055 | 6.46882207 |

N.D.: Not Determined

Example 5. Analysis of Anti-Fungal Effects of KBL693

The anti-fungal effect of KBL693 was confirmed by a spot assay method. About 1% of KBL693 was inoculated on MRS liquid medium, and then was incubated in the 37° C. incubator for about 24 hours under anaerobic conditions for stationary culturing. The culture solution in which the cells were incubated was spotted in the MRS solid medium, which was prepared under anaerobic conditions, in an amount of 10 μL at each time, and then incubated at 37° C. under anaerobic conditions for about 24 hours. *Malassezia furfur* KCTC 7545, a fungal microorganism, was prepared by inoculating it in the mYPG liquid medium, which was prepared under aerobic conditions, at a rate of 1% and followed by incubation in the 37° C. incubator for about 24 to 48 hours. The mYPG soft medium to be used for anti-fungal efficacy evaluation was prepared with the components shown in Table 4, and 2.5 mL of the prepared culture medium was inoculated with the culture solution in which 500 μL of *M. furfur* was incubated. 2.5 mL of mYPG soft medium inoculated with *M. furfur* was poured into the MRS medium spotted with KBL693 and dried for 1 hour. The dried medium was incubated under aerobic conditions in the 37° C. incubator for 24 to 48 hours. When a clear zone was identified in the cultured medium, anti-fungal activity was determined by measuring the length from the outside of the spotted lactic acid bacteria to the clear zone. The clear zone is a part where growth of fungi was inhibited, and the anti-fungal activity caused by lactic acid bacteria was determined through the length to the clear zone.

Figure 8:
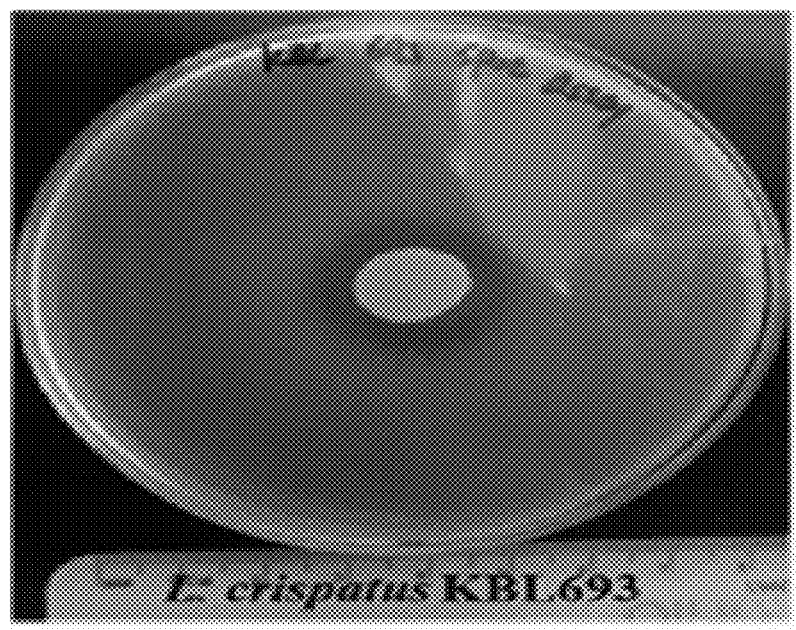
FIG. 8 illustrates the result of a spot assay confirming the anti-fungal activity of Lactobacillus crispatus KBL693 strain.

As a result of three repeated experiments, the clear zones were identified at intervals of about 4.33 mm at the part spotted with KBL693 (FIG. 8), which indicates that KBL693 can effectively suppress the growth of fungal microorganisms.

TABLE 4

| Components | Proportion (g/l) |
| --- | --- |
| Malt extract | 5.0 |
| Peptone | 10.0 |
| Glucose | 20.0 |
| Tween 40 | 1.0 |
| Tween 80 | 1.0 |
| Agar | 4.5 |

Example 6. Effects of KBL693 on Alleviation of Atopic Conditions

Based on a comprehensive review of the in vitro screening test results, the animal tests were conducted by selecting *Lactobacillus crispatus* KBL692, KBL693, and KBL702 which had the most excellent immunoregulatory effect. In order to verify the effect on atopic alleviation among the allergy improvement effects of KBL693, the NC/Nga mouse model, an animal model of atopic skin disease, was used.

After dividing NC/Nga mice into groups of five mice, the back of each mouse was epilated from the lower ear to the upper tail and mice were left for 24 hours. Then, 200 µL of a 1% DNCB (dinitrochlorobenzene) solution (acetone:olive oil=3:1) was applied twice a week onto the epilated portion to induce atopic dermatitis. From the third week of dermatitis induction, 200 µL of PBS was orally administered to the mice in the control group daily; the cultured test strain was centrifuged, washed through dilution with PBS and recovery, and then prepared so that at least $2\times10^9$ CFU could be added to 200 µL of PBS, which was orally administered to the mice in the test group in 200 µL/day. Meanwhile, 200 µL of dexamethasone (60 µg/mL) was administered to the mice in the positive control group. Then, during three weeks of administration of the bacteria, dermatitis scores of the mice in the control and test groups were measured weekly, and on the 3rd week after the administration of the bacteria, the mouse's scratching time and skin thickness were measured.

6-1. Evaluation of Dermatitis Score

To evaluate DNCB-induced skin lesions, the dermatitis score was measured through the following method. Skin conditions were monitored by taking pictures for 3 weeks at one week intervals from the 3rd week since the strain was administered. Four indicators of dryness, edema, erythema/hemorrhage, and erosion/excoriation of the skin were checked. And a condition with no lesions was scored as point 0, a mild condition as point 1, a moderate condition as point 2, and a severe condition as point 3, and the total score was evaluated.

Figure 9:
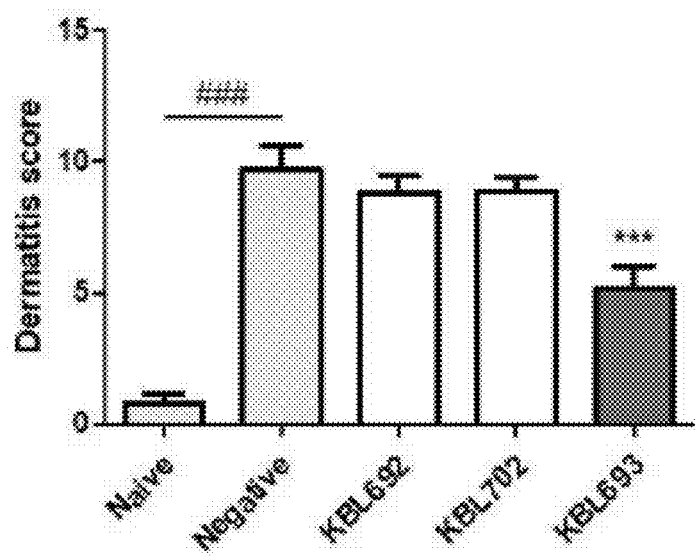
FIG. 9 illustrates the result confirming the dermatitis score reducing effect by the oral administration of Lactobacillus crispatus KBL693 stain to mouse models that atopic dermatitis was induced.

As a result, as shown in FIG. 9, the dermatitis score induced by DNCB was significantly reduced in the group dosed with KBL693, compared to the control group (negative) where atopic dermatitis was induced and the groups dosed with other *Lactobacillus crispatus* strains. As a result, the effect of treating atopic dermatitis according to the administration of KBL693 was verified.

6-2. Itching Relief Effects

In order to verify the effect of alleviating itching according to the administration of KBL693 in the mouse models suffering from atopic dermatitis induced by DNCB, the scratching time was measured by taking a video of the mouse models for 10 minutes after 3 weeks of strain administration.

Figure 10:
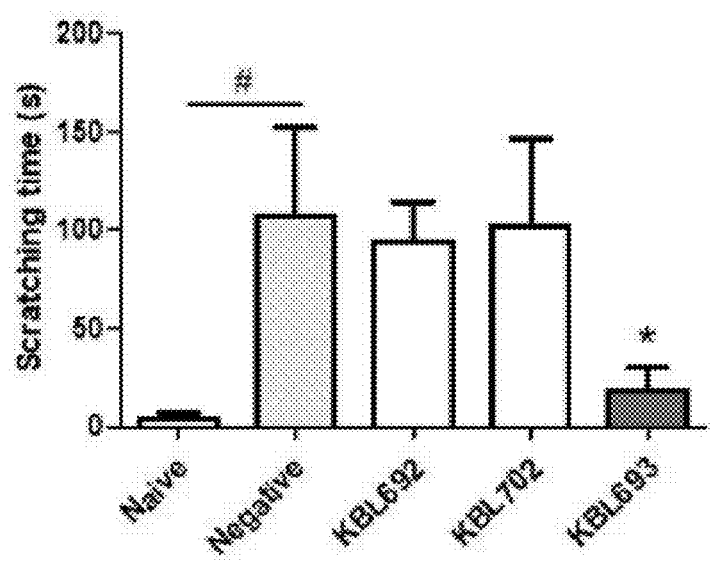
FIG. 10 illustrates the result confirming the itching-alleviating effect by the oral administration of Lactobacillus crispatus KBL693 strain to mouse models that atopic dermatitis was induced.

As a result, as can be seen in FIG. 10, it appeared that the scratching time was significantly reduced in the test group that KBL693 was administered, compared to the control group (negative) where atopic dermatitis was induced and the groups dosed with other *Lactobacillus crispatus* strains, which confirmed that the itching symptoms of atopic dermatitis were much alleviated by the administration of KBL693.

6-3. Decrease of Skin Thickness

In order to verify the effect of alleviating itching after administration of KBL693 to mouse models suffering from atopic dermatitis induced by DNCB, the mouse ear thickness and dorsal skin thickness were measured with calipers three weeks after the strain was administered, and the relief of edema symptom due to atopic dermatitis was observed.

Figure 11:
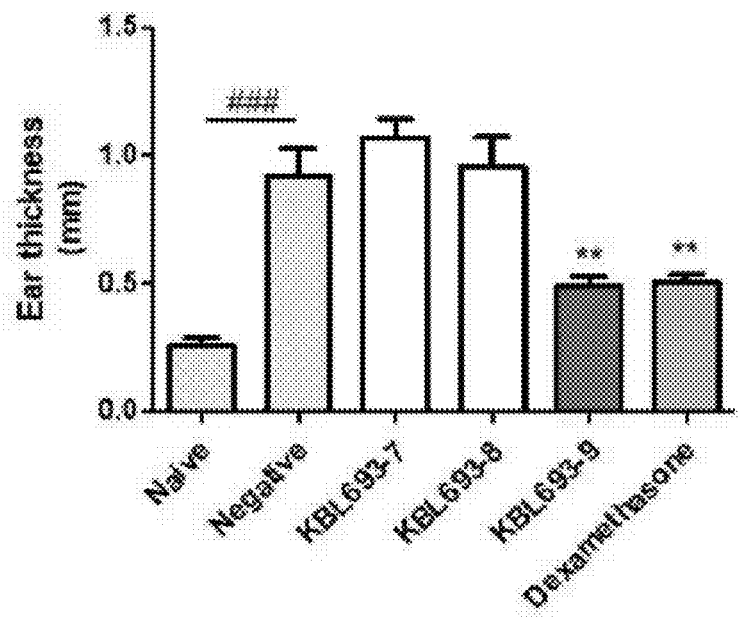
FIG. 11 illustrates the result confirming the ear thickness lowering effect by the oral administration of Lactobacillus crispatus KBL693 strain to mouse models that atopic dermatitis was induced.
Figure 12:
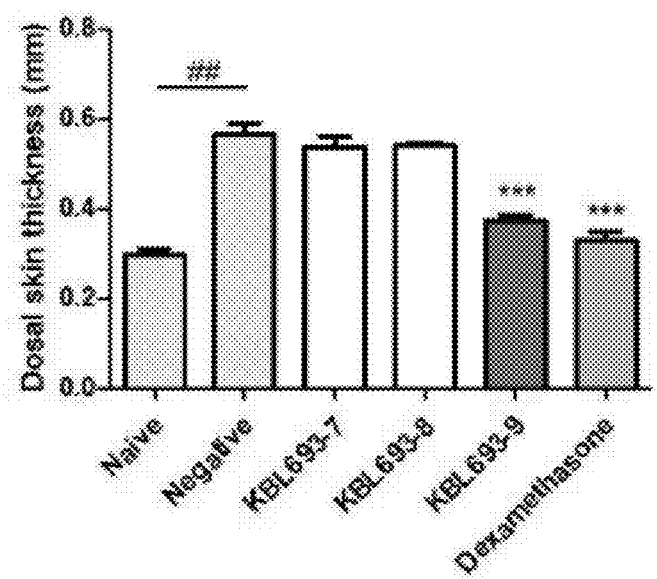
FIG. 12 illustrates the result confirming the skin thickness lowering effect by the oral administration of Lactobacillus crispatus KBL693 strain to mouse models that atopic dermatitis was induced.

As a result, as can be seen in FIGS. 11 and 12, it was observed that in the test group dosed with KBL693 and the positive control group, the ear and dorsal skin thicknesses were significantly reduced. In FIGS. 11 and 12, 693-7, 693-8 and 693-9, respectively, mean the test groups that KBL693 was prepared so that at least $2\times10^7$, $2\times10^8$, and $2\times10^9$ CFU could be added to 200 µL of PBS, which were orally administered to the mice in the test group in 200 µL/day.

Example 7. Effects of KBL693 on Treatment and Prevention of Asthma in Mouse Models of Ovalbumin (OVA)-Induced Asthma In order to verify the effect of KBL693 (LC206) on allergic asthma, mouse models of OVA-induced asthma were prepared as follows, conducted a histopathological examination and assessed the expression level of IL-5 and IL-13.

7-1. Preparation of Mouse Models of OVA-Induced Asthma

Five-week old Balb/c mice having the average weight of about 15 g were subjected to acclimation for one week, and then the mice which did not show abnormality under the basic physical examination were selected. As shown in FIG. 13A, the mice to be used were classified into the normal control group (Control-PBS; no OVA administered or inhaled; n=8), asthma-induced control group (OVA-PBS; OVA administered or inhaled; n=9), and test group (OVA-LC206; n=8). Before the mice were sacrificed on the 31$^{st}$ day from the start of the experiment, 200 µL of PBS was administered orally to the normal control group and the asthma-induced control group daily, and 200 µL of KBL693 diluted in PBS to be at least $2\times10^9$ CFU/0.2 mL was administered orally to the test group daily.

Sensitization was performed by intraperitoneal injecting 200 µL of a phosphate buffer (pH 7.4) in which 2 mg of aluminum hydroxide (Imject™ Alum Adjuvant, Thermofisher) and 20 µg of OVA (Ovalbumin, Sigma-aldrich) was suspended, to the mice one week later (D7) and three weeks later (D21) after the acclimation for one week, respectively. From 28th day to 30th day from the start of the experiment, 1% of OVA was inhaled to lungs through intranasal administration (three challenges). Pentobarbital was administered when 24 hours elapsed after the last challenge (D31), and then a bronchial incision was performed to collect lung tissue samples.

7-2. Histopathological Examination

Infiltration of inflammatory cells consisting of eosinophils, neutrophils and macrophages can be observed in the bronchi in which the antigen is treated. Thus, in order to verify the effect of KBL693 on asthma, a histopathological examination of lung tissue samples of each group obtained in Example 7-1 was performed. The lung tissue samples obtained in Example 7-1 were prepared into 4 µm-thick tissue sections through conventional formalin fixed paraffin embedded (FFPE) tissue section procedure, and then conducted H&E staining with hematoxylin and Eosin Y (Eosin Y; ThermoShandon, Pittsburgh, Pa.). After H&E staining, tissue sections of each group were observed with an optical microscope (FIGS. 13B-D).

As a result, as shown in FIGS. 13B-D, in the asthma-induced control group (OVA-PBS), many inflammatory cells including eosinophils were infiltrated around the bronchioles, and hyperproliferated epithelial cells and thickened bronchial smooth muscle were also found. On the other hand, in the test group dosed with KBL693 (OVA-LC206), infiltration of inflammatory cells including eosinophils was significantly reduced, the thickness of the bronchial tissue was reduced, and epithelial cells were hardly damaged. As a result, the therapeutic effect of KBL693 on OVA-induced allergic asthma was confirmed.

7-3. Assay of Expression Level of Total IL-5 and Total IL-13

A flow cytometer (LSRFortessa X-20, BD) was used to evaluate immunocytes in lungs from the lung tissue samples collected from each group. To stain IL-5$^+$CD4$^+$ T, IL-13$^+$CD4$^+$ T cells, antibodies to several markers (Anti-Mouse CD45, BioLegend; Anti-Mouse CD3c, BD; Anti-Mouse/Human IL-5, BioLegend; Anti-Mouse IL-13, Invitrogen) were used. IL-5$^+$ and IL-13$^+$ cells were determined by counting the cells producing IL-5 or IL-13, among lymphocytes having CD45 and CDε as markers (FIG. 14A).

As a result, as shown in FIGS. 14A-14D, it was found that IL-5 and IL-13 levels in the mice of the asthma-induced control group (OVA-PBS) were significantly increased compared to the normal control group (PBS), while the level of total IL-5 and total IL-13 in the mice of the test group dosed with KBL693 (OVA-KBL693) were significantly decreased compared to the asthma-induced control group. Accordingly, it was found that KBL693 of the present invention could provide therapeutic and preventive effects on allergic asthma through inhibition of secretion of IL-5 and IL-13 which are Th2 type cytokines that mediate allergic reactions.

Example 8. Effects of KBL693 on Treatment and Prevention of Asthma in Models of House Dust Mite (HDM)-Induced Asthma House dust mites are the allergen which is the leading cause of extrinsic asthma. In order to verify the effect of KBL693 on allergic asthma, mouse models of HDM-induced asthma were prepared as follows, an airway hypersensitivity was evaluated, and the proportion of eosinophils in CD45$^+$ cells, the proportion of IL-5$^+$CD4 T cells in CD4$^+$ T cells, and the proportion of IL-13$^+$CD4 T cells in CD4$^+$ T cells were determined.

8-1. Preparation of Mouse Models of HDM-Induced Asthma

Five-week old Balb/c mice having the average weight of about 15 g were subjected to acclimation for one week, and then the mice which did not show abnormality under the basic physical examination were selected. The mice to be used were classified into the normal control group (Control-PBS; no HDM administered), asthma-induced control group (HDM-PBS; HDM administered), and test group (HDM-KBL693), and five mice per each group were used to evaluate the airway hyperresponsiveness (AHR), and eight mice per each group were used to evaluate immunocytes in lungs.

Sensitization was performed by intranasal administering 50 μL of a phosphate buffer (pH 7.4) in which 10 μg of HDM (Greer) was suspended, to the mice one week later (D7) after the acclimation for one week. One week later since the sensitization, 50 μL of a phosphate buffer in which 10 μg of HDM was suspended was inhaled to lungs via intranasal administration, for five days (D14~D18) (five challenges). Pentobarbital was administered when 24 hours elapsed after the last challenge (D19), and then the airway hyperresponsiveness (AHR) was evaluated (Example 8-2), and a bronchial incision was performed to collect lung tissue samples.

8-2. Evaluation of AHR

A mouse anesthetized by administration of pentobarbital was connected to an AHR meter (FinePointe Resistance and Compliance, DSI-Buxco), and various concentrations of methacholine dissolved in PBS (0, 5, 10, 20 and 40 mg/mL) were administered thereto. Then, the AHR value was calculated by measuring the volume of air passing through the airway (FIG. 15).

Figure 15:
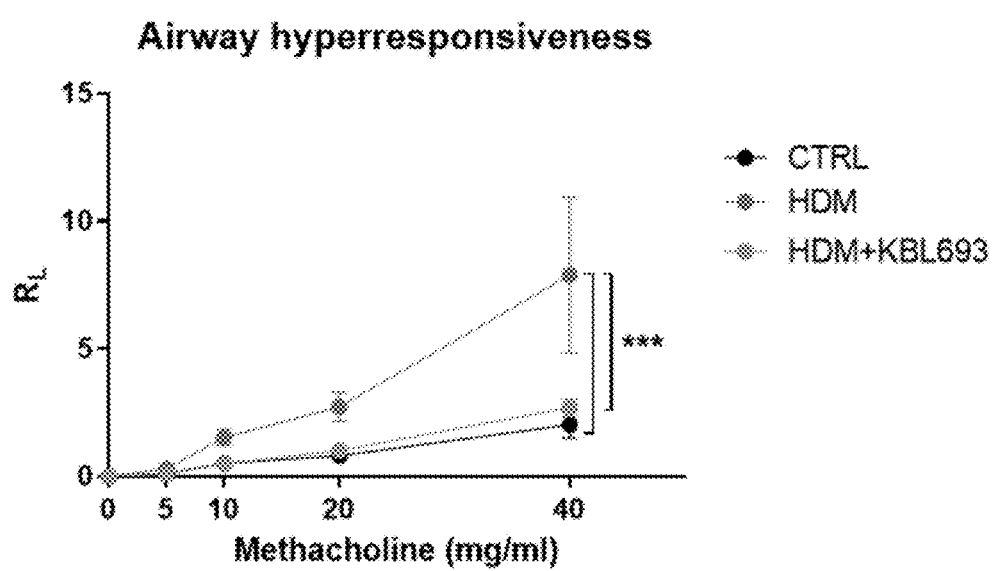
FIG. 15 illustrates the result confirming the airway hyper-responsiveness (AHR) reducing effect by Lactobacillus crispatus KBL693 strain administered to mouse models with house dust mite (HDM)-induced asthma.

As a result, as shown in FIG. 15, it was confirmed that, as the concentration of methacholine increased, AHR ($R_L$) was slowly increased in the normal control group (CTRL), while AHR was rapidly increased in the asthma-induced control group (HDM). On the other hand, in the test group dosed with KBL693 (HDM+KBL693), AHR was significantly reduced compared to the asthma-induced group (HDM) over the entire concentrations of methacholine. This difference was more obvious when administered with high concentrations of methacholine than with low concentrations of methacholine. Accordingly, it was found that KBL693 could effectively inhibit AHR which causes asthma, and thus could effectively be used for the treatment and prevention of allergic asthma.

8-3. Determination of the Proportion of Eosinophils in CD45$^+$ Cells, the Proportion of IL-5$^+$CD4 T Cells in CD4$^+$ T Cells, and the Proportion of IL-13$^+$CD4 T Cells in CD4$^+$ T Cells A flow cytometer (LSRFortessa X-20, BD) was used to evaluate immunocytes in lungs. To stain eosinophil and IL-5$^+$CD4$^+$ T, IL-13$^+$CD4$^+$ T cells, antibodies to several markers (Anti-Mouse CD45, BioLegend; Rat Anti-Mouse Siglec-F, BD; Anti-Mouse CD11b, BD; Anti-Mouse CD3c, BD; Anti-Mouse TCRβ, BioLegend; Anti-Mouse CD4, BioLegend; Anti-Mouse/Human IL-5, BioLegend; Anti-Mouse IL-13, Invitrogen) were used. Eosinophil were determined by counting Siglec-f$^+$CD11b$^+$ cells, among the cells expressing CD45, a common leucocyte marker, and IL-5$^+$CD4$^+$ T, IL-13$^+$CD4$^+$ T cells were determined by counting the cells of producing IL-5 or IL-13, among CD4$^+$ T cells having CDε, TCRβ, and CD4 as markers (FIGS. 16A-C).

Figures 16A, 16B, 16C:
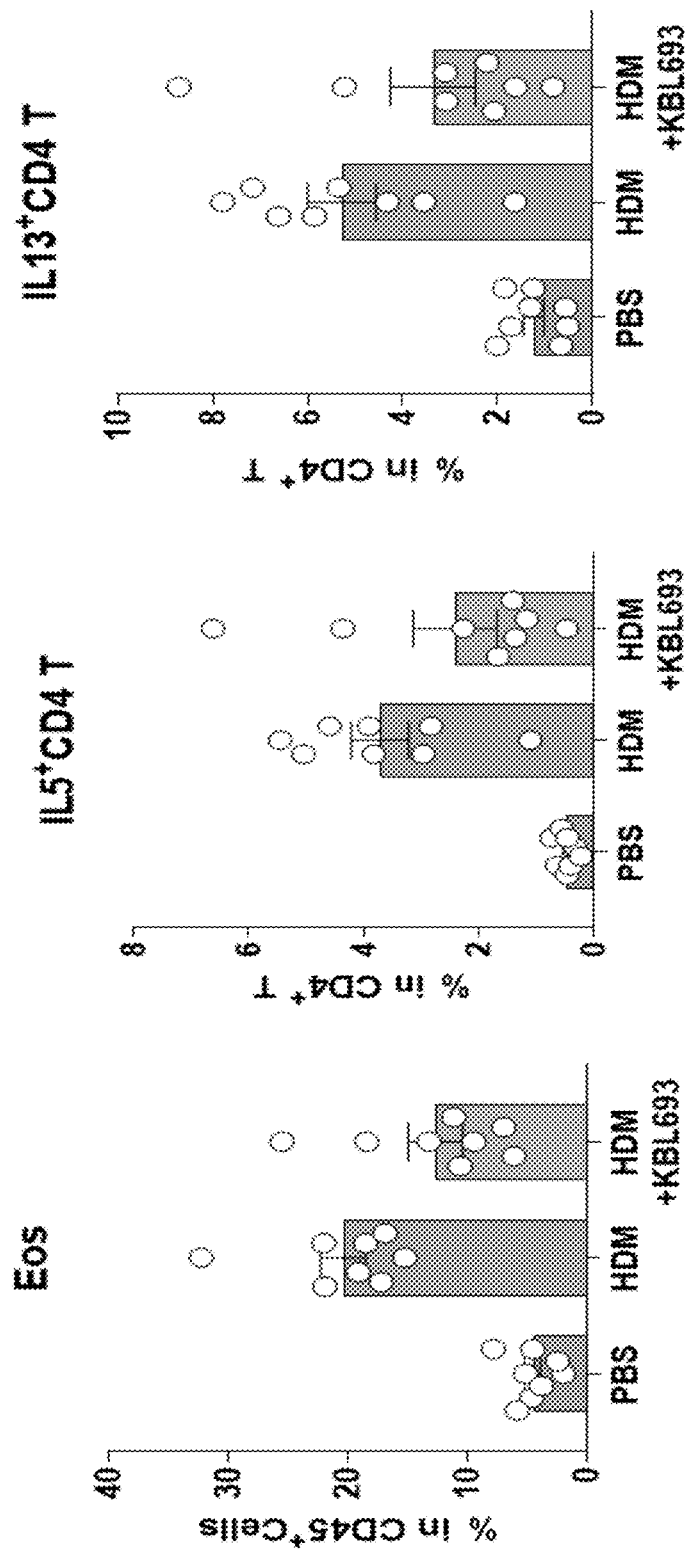
FIGS. 16A-16C illustrates the result confirming the effect of reducing eosinophils, IL-5$^+$ CD4 T cells and IL-13$^+$ CD4 T cells by the administration of Lactobacillus crispatus KBL693 strain.

As a result, as shown in FIGS. 16A-16C, it was confirmed that, in the case of the asthma-induced control group (HDM), the proportions of immunocytes, i.e., eosinophils, IL-5$^+$CD4 T cells and IL-13$^+$CD4 T cells were all significantly increased compared to the normal control group (PBS), while in the case of the test group dosed with KBL693 (HDM+KBL693), the proportions of eosinophils, IL-5$^+$CD4 T cells and IL-13$^+$CD4 T cells were all significantly decreased compared to the asthma-induced control group. Accordingly, it was found that KBL693 could provide therapeutic and preventive effects on allergic asthma through inhibition of the inflammatory cells, i.e., eosinophils, IL-5$^+$CD4 T cells and IL-13$^+$CD4 T cells.

Specific aspects of the present invention have been described in detail above, and it is obvious to those skilled in the art that these specific aspects are only preferred embodiments, and the scope of the present invention is not limited thereby. Therefore, the scope of the present invention is substantially defined by the following claims, with equivalents to the claims Name of Depository Organization:

Korean Collection for Type Cultures, Korea Research Institute of Bioscience and Biotechnology (KRIBB), 181, Ipsin-gil, Jeongeup-si, Jeollabuk-do, 56212, Republic of Korea.

Accession No.:

KCTC13519BP

Accession Date:

2018 Apr. 27

INDUSTRIAL APPLICABILITY

The *Lactobacillus crispatus* KBL693 strain (Accession No. KCTC 13519BP) according to the present invention attenuates allergic reactions of cells, significantly improves symptoms of atopic dermatitis, and exhibits anti-inflammatory, immunoregulatory and anti-fungal effects. Thus, the single strain alone can achieve all the purposes of alleviating allergic diseases and improving inflammatory diseases and autoimmune diseases, thereby finding advantageous applications as a probiotic substance. In addition, the strain, based on the anti-fungal activity thereof, can be advantageously utilized in a skin external preparation against various skin diseases caused by fungi, and in a cosmetic composition and a functional patch for alleviating sensitive skin.

SEQUENCE LIST FREE TEXT

An electronic file attached

The invention claimed is:

1. A composition in the form of a capsule or tablet comprising effective dose of at least one selected from strain of *Lactobacillus crispatus* KBL693 with Accession No. KCTC 13519BP, culture of said strain and lysate of said strain.

2. The composition according to claim 1, wherein the strain, culture of said strain and lysate of said strain are lyophilized.

3. The composition according to claim 1, wherein the effective dose is sufficient for alleviation of allergic symptoms, alleviation of inflammatory symptoms and immunoregulation.

4. The composition according to claim 3, wherein said allergic symptoms are selected from eczema, allergic asthma, allergic rhinitis, atopic dermatitis, allergic conjunctivitis or food allergy.

5. The composition according to claim 1, wherein the composition is an anti-fungal composition exhibiting anti-fungal activities to fungi of the genus *Malassezia*.

6. The composition according to claim 5, wherein said composition exhibits anti-fungal activities to *Malassezia furfur*.

7. A skin external preparation comprising at least one selected from strain of *Lactobacillus crispatus* KBL693 with Accession No. KCTC 13519BP, culture of said strain and lysate of said strain, wherein the skin external preparation is in the form of cream, pack, lotion, essence, foundation or makeup base.

8. A patch comprising at least one selected from a strain of *Lactobacillus crispatus* KBL693 with Accession No. KCTC 13519BP, cultures of said strain and lysates of said strain.

9. The composition according to claim 1, wherein the effective dose is sufficient for the treatment of allergic disease, inflammatory disease, or autoimmune disease, wherein the treatment is defined as at least one of inhibiting the growth of the disease, alleviating the disease and palliating the symptom of the disease.

10. The composition according to claim 9, wherein said allergic disease is eczema, allergic asthma, allergic rhinitis, atopic dermatitis, allergic conjunctivitis or food allergy.

11. The composition according to claim 9, wherein said inflammatory or autoimmune disease is rheumatoid arthritis, rheumatic fever, lupus, systemic scleroderma, atopic dermatitis, psoriasis, psoriatic arthritis, asthma, Guilian-Barre syndrome, myasthenia gravis, dermatomyositis, polymyositis, multiple sclerosis, autoimmune encephalomyelitis, polyarteritis *nodosa*, Hashimoto's thyroiditis, temporal arteritis, juvenile diabetes, alopecia areata, pemphigus, aphthous stomatitis, autoimmune hemolytic anemia, Wegener's granulomatosis, Sjogren's syndrome, Addison's disease, Crohn's disease, Behcet's disease, edema, conjunctivitis, periodontitis, rhinitis, otitis media, chronic sinusitis, pharyngolaryngitis, tonsillitis, bronchitis, pneumonia, gastric ulcer, gastritis, colitis, gout, eczema, acne, contact dermatitis, seborrheic dermatitis, ankylosing spondylitis, fibromyalgia, osteoarthritis, peri-arthritis of the shoulder, tendinitis, tenosynovitis myositis, hepatitis, cystitis, nephritis, sepsis, vasculitis or bursitis.

12. A method for treating allergic disease, inflammatory disease or autoimmune disease, comprising administering the composition according to claim 1, to a subject in need thereof, wherein the treating is defined as at least one of inhibiting the growth of the disease, alleviating the disease and palliating the symptom of the disease.

13. The preparation according to claim 7, wherein the strain, culture of said strain and lysate of said strain are lyophilized.

14. The patch according to claim 8, wherein the patch is a medical patch for improving cutaneous allergy, skin urticaria, atopic dermatitis, psoriasis, mycotic infection or eczema.

15. The patch according to claim 8, wherein the patch is a cosmetic patch for improving cutaneous allergy, skin urticaria, atopic dermatitis, psoriasis, mycotic infection or eczema.

* * * * *

```
                        SEQUENCE LISTING

<160> NUMBER OF SEQ ID NOS: 1

<210> SEQ ID NO 1
<211> LENGTH: 1470
<212> TYPE: DNA
<213> ORGANISM: Lactobacillus crispatus

<400> SEQUENCE: 1
cgcggggtgg cgcgagctat aatgcagtcg agcgagcgga actaacagat ttacttcggt      60
aatgacgtta ggaaagcgag cggcggatgg gtgagtaaca cgtggggaac ctgccccata     120
gtctgggata ccacttggaa acaggtgcta ataccggata agaaagcaga tcgcatgatc     180
agcttttaaa aggcggcgta agctgtcgct atgggatggc cccgcggtgc attagctagt     240
tggtaaggta aaggcttacc aaggcgatga tgcatagccg agttgagaga ctgatcggcc     300
acattgggac tgagacacgg cccaaactcc tacgggaggc agcagtaggg aatcttccac     360
aatggacgca agtctgatgg agcaacgccg cgtgagtgaa gaaggttttc ggatcgtaaa     420
gctctgttgt tggtgaagaa ggatagaggt agtaactggc ctttatttga cggtaatcaa     480
ccagaaagtc acggctaact acgtgccagc agccgcggta atacgtaggt ggcaagcgtt     540
gtccggattt attgggcgta aagcgagcgc aggcggaaga ataagtctga tgtgaaagcc     600
ctcggcttaa ccgaggaact gcatcggaaa ctgttttttct tgagtgcaga agaggagagt     660
ggaactccat gtgtagcggt ggaatgcgta gatatatgga agaacaccag tggcgaaggc     720
ggctctctgg tctgcaactg acgctgaggc tcgaaagcat gggtagcgaa caggattaga     780
taccctggta gtccatgccg taaacgatga gtgctaagtg ttgggaggtt tccgcctctc     840
agtgctgcag ctaacgcatt aagcactccg cctggggagt acgaccgcaa ggttgaaact     900
caaaggaatt gacgggggcc cgcacaagcg gtggagcatg tggtttaatt cgaagcaacg     960
cgaagaacct taccaggtct tgacatctag tgccatttgt agagatacaa agttcccttc    1020
ggggacgcta agacaggtgg tgcatggctg tcgtcagctc gtgtcgtgag atgttgggtt    1080
aagtcccgca acgagcgcaa cccttgttat tagttgccag cattaagttg ggcactctaa    1140
tgagactgcc ggtgacaaac cggaggaagg tgggatgac gtcaagtcat catgcccctt    1200
atgacctggg ctacacacgt gctacaatgg gcagtacaac gagaagcgag cctgcgaagg    1260
caagcgaatc tctgaaagct gttctcagtt cggactgcag tctgcaactc gactgcacga    1320
agctggaatc gctagtaatc gcggatcagc acgccgcggt gaatacgttc ccgggccttg    1380
tacacaccgc ccgtcacacc atgggagtct gcaatgccca agccggtgg cctaaccttc    1440 ggaaggagcc gtctaagtag acaatgtgca                                    1470
```